(12) United States Patent
Mozhdehi

(10) Patent No.: US 11,884,941 B2
(45) Date of Patent: Jan. 30, 2024

(54) NON-CANONICAL LIPOPROTEINS WITH PROGRAMMABLE ASSEMBLY AND ARCHITECTURE AND METHOD OF MAKING NON-CANONICAL LIPOPROTEINS

(71) Applicant: Davoud Mozhdehi, Syracuse, NY (US)

(72) Inventor: Davoud Mozhdehi, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 17/529,860

(22) Filed: Nov. 18, 2021

(65) Prior Publication Data
US 2022/0154151 A1    May 19, 2022

Related U.S. Application Data

(60) Provisional application No. 63/115,696, filed on Nov. 19, 2020.

(51) Int. Cl.
*C12P 7/64* (2022.01)
*C12N 9/10* (2006.01)

(52) U.S. Cl.
CPC .............. *C12N 9/1029* (2013.01); *C12P 7/64* (2013.01); *C12Y 203/01097* (2013.01)

(58) Field of Classification Search
CPC .......... C12N 9/1029; C12P 7/64; C12P 21/02; C12Y 203/01097
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013).*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Hossain et al., Chem. Commun. 56:10281-10284, Sep. 14, 2020.*
Zhao et al., Advance Science 8, pp. 1-10, 2021.*
Heal et al., Organic & Biomolecular Chemistry 6(13):2217-2444, 2008.*

* cited by examiner

*Primary Examiner* — Delia M Ramirez
(74) *Attorney, Agent, or Firm* — Bond Schoeneck & King PLLC; David L. Nocilly

(57) ABSTRACT

Artificial lipoproteins bearing non-canonical post-translational modifications that are synthesized by leveraging substrate promiscuity of an acyltransferase. The non-canonical functionality of these lipoprotein results in a distinctive hysteretic assembly that is absent from the canonical lipoproteins and is used to prepare hybrid multiblock materials with precise and programmable patterns of amphiphilicity due to the unique assembly and function of the non-canonical post-translational modifications.

8 Claims, 22 Drawing Sheets
Specification includes a Sequence Listing.

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: substrate for transferase

<400> SEQUENCE: 1

Gly Leu Tyr Ala Ser Lys Leu Phe Ser Asn Leu
1               5                   10

<210> SEQ ID NO 2
<211> LENGTH: 426
```

<210> TYPE: PRT
<213> ORGANISM: Artificial Sequence
<220> FEATURE:
<223> OTHER INFORMATION: intrinsically disordered peptide-polymer

<400> SEQUENCE: 2

```
Gly Val Gly Val Pro Gly Val Gly Val Pro Gly Ala Gly Val Pro Gly
1               5                   10                  15

Val Gly Val Pro Gly Val Gly Val Pro Gly Val Gly Val Pro Gly Val
            20                  25                  30

Gly Val Pro Gly Ala Gly Val Pro Gly Val Gly Val Pro Gly Val Gly
        35                  40                  45

Val Pro Gly Gly Lys Gly Val Gly Val Pro Gly Val Gly Val Pro Gly
50                  55                  60

Ala Gly Val Pro Gly Val Gly Val Pro Gly Val Gly Val Pro Gly Val
65                  70                  75                  80

Gly Val Pro Gly Val Gly Val Pro Gly Ala Gly Val Pro Gly Val Gly
                85                  90                  95

Val Pro Gly Val Gly Val Pro Gly Gly Lys Gly Val Gly Val Pro Gly
            100                 105                 110

Val Gly Val Pro Gly Ala Gly Val Pro Gly Val Gly Val Pro Gly Val
        115                 120                 125

Gly Val Pro Gly Val Gly Val Pro Gly Val Gly Val Pro Gly Ala Gly
    130                 135                 140

Val Pro Gly Val Gly Val Pro Gly Val Gly Val Pro Gly Gly Lys Gly
145                 150                 155                 160

Val Gly Val Pro Gly Val Gly Val Pro Gly Ala Gly Val Pro Gly Val
                165                 170                 175

Gly Val Pro Gly Val Gly Val Pro Gly Val Gly Val Pro Gly Val Gly
            180                 185                 190

Val Pro Gly Ala Gly Val Pro Gly Val Gly Val Pro Gly Val Gly Val
        195                 200                 205

Pro Gly Gly Lys Gly Val Gly Val Pro Gly Val Gly Val Pro Gly Ala
    210                 215                 220

Gly Val Pro Gly Val Gly Val Pro Gly Val Gly Val Pro Gly Val Gly
225                 230                 235                 240

Val Pro Gly Val Gly Val Pro Gly Ala Gly Val Pro Gly Val Gly Val
                245                 250                 255

Pro Gly Val Gly Val Pro Gly Gly Lys Gly Val Gly Val Pro Gly Val
            260                 265                 270

Gly Val Pro Gly Ala Gly Val Pro Gly Val Gly Val Pro Gly Val Gly
        275                 280                 285

Val Pro Gly Val Gly Val Pro Gly Val Gly Val Pro Gly Ala Gly Val
    290                 295                 300

Pro Gly Val Gly Val Pro Gly Val Gly Val Pro Gly Gly Lys Gly Val
305                 310                 315                 320

Gly Val Pro Gly Val Gly Val Pro Gly Ala Gly Val Pro Gly Val Gly
                325                 330                 335

Val Pro Gly Val Gly Val Pro Gly Val Gly Val Pro Gly Val Gly Val
            340                 345                 350

Pro Gly Ala Gly Val Pro Gly Val Gly Val Pro Gly Val Gly Val Pro
        355                 360                 365

Gly Gly Lys Gly Val Gly Val Pro Gly Val Gly Val Pro Gly Ala Gly
    370                 375                 380
```

-continued

```
Val Pro Gly Val Gly Val Pro Gly Val Gly Val Pro Gly Val Gly Val
385                 390                 395                 400

Pro Gly Val Gly Val Pro Gly Ala Gly Val Pro Gly Val Gly Val Pro
                405                 410                 415

Gly Val Gly Val Pro Gly Gly Lys Gly Tyr
            420             425
```

NON-CANONICAL LIPOPROTEINS WITH PROGRAMMABLE ASSEMBLY AND ARCHITECTURE AND METHOD OF MAKING NON-CANONICAL LIPOPROTEINS

CROSS-REFERENCE TO RELATED APPLICATION

The present application claims priority to US Provisional Applicant No. 63/115,696, filed on Nov. 19, 2020 hereby incorporated by reference in its entirety.

BACKGROUND OF THE INVENTION

1. Field of the Invention

The present invention relates to artificial lipoproteins and, more specifically, to an approach for synthesizing artificial lipoproteins using the substrate promiscuity of an acyltransferase and artificial lipoproteins synthesized using that approach.

2. Description of the Related Art

Proteins are sequence-defined polymers with applications in healthcare, nano-, and biotechnology. The desired function is often encoded in protein sequence by incorporating structural (fold-ed) motifs. However, many proteins contain intrinsically disordered regions (IDRs) without a well-defined structure. The consensus sequences of IDRs are used to design recombinant intrinsically disordered peptide-polymers (IDPPs) for mimicking the structure-function of these biomaterial. Given the lack of well-defined secondary and tertiary interactions in IDPPs, programming their hierarchical assembly is often achieved by designing chimeric sequences using recombinant or semisynthetic methods to fuse two regions with different hydrophobicity or structural order, akin to self-assembly of block copolymers. However, the chemical (and functional) design space of chimeric IDPPs produced by genetic engineering is restricted to amino acid-like constituents due to constraints of translational machinery.

Post-translational modifications (PTMs) involve the addition of non-proteogenic motifs to proteins after translation. For example, modification of short peptides and IDPPs with lipids can be used to drive the assembly of hybrid amphiphiles into nanoparticles, given the difference in the hydrophobicity of the polypeptide chain and the lipid group. However, the repertoire of lipids in biology is evolutionarily constrained. The canonical lipidation machinery catalyses the transfer of only a few types of lipids (saturated and unsaturated fatty acids, sterols, etc.) to substrate proteins. Though "non-natural" lipidated proteins can be produced via chemoenzymatic methods, these approaches are technically challenging, time-consuming, and expensive. Alternatively, biosynthetic routes can address these limitations if their narrow substrate scope is expanded by a combination of metabolic and protein engineering. Accordingly, there is a need in the art for an approach that can be used to produce non-natural lipoproteins.

BRIEF SUMMARY OF THE INVENTION

The present invention may be used to produce non-naturally occurring lipoproteins using the substrate promiscuity of the post-translational modification machinery to modify proteins with artificial fatty acids to form lipoproteins bearing a non-canonical post-translational modification. In a first embodiment, the present invention is a method of synthesizing a non-naturally occurring lipoprotein, comprising the steps of coexpressing a lipid modification enzyme with an intrinsically disordered peptide-polymer fused to a peptide substrate of the lipid modification enzyme and supplementing the expression media with a fatty acid. The lipid modification enzyme may comprise N-myristoyl transferase. The peptide substrate may comprise SEQ. ID NO: 1. The fatty acid may comprise 12-azidododecanoic acid. The intrinsically disordered peptide-polymer may comprise SEQ. ID. NO: 2. In another embodiment, the invention comprises a non-naturally occurring lipoprotein, comprising an intrinsically disordered peptide-polymer fused to a fatty acid. The fatty acid may be 12-azidododecanoic acid. The intrinsically disordered peptide-polymer may comprise SEQ. ID. NO: 2.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic showing the substrate promiscuity of biological PTM machinery is used to produce lipoproteins modified with an artificial lipid, where panel a) shows a one-pot approach involves co-expression of the NMT enzyme with a protein substrate while supplementing the expression media with an artificial lipid (ADA). The plasmid encodes for 1) the yeast NMT, 2) an elastin-derived IDPP, as a model hydrophilic peptide-polymer, fused to a short peptide substrate of NMT. Panel b) shows lipoproteins prepared using canonical PTM (M-IDPP) and non-canonical PTM (ADA-IDPP) are 99.4% identical with only small perturbation in the terminal region of each lipid (boxed structure);

FIG. 2 is a pair of graphs showing molecular characterization confirms the incorporation of ADA using the bicistronic vector, where graph a) shows that only ADA-IDPP reacts with a fluorophore bearing a dibenzocyclooctyne (DBCO), and graph b) shows that analytical RP-HPLC confirms the increased hydrophobicity of ADA-IDPP compared to the unmodified IDPP. Since ADA is less hydrophobic compared to myristic acid, ADA-IDPP elutes earlier than M-IDPP;

FIG. 3 is a series of graphs of temperature-programmed turbidimetry was used to monitor the LCST phase transition of IDPP (a), ADA-IDPP(b), and M-IDPP(c). Graph d) shows that the partial phase diagram for the three constructs, showing the boundaries between the single- and the two-phase region. The dashed lines represent the 90% confidence interval of the line fitted to observed Tt, Table 3. IDPP exhibits a reversible LCST phase transition, characterized by a sharp increase in the turbidity of the solution above $T_t$ and sharp concentration dependence of $T_t$. Modification with M or ADA modulates IDPP phase behavior. Only ADA-IDPP exhibits a unique "shoulder" in the turbidity profiles during the cooling cycle (inset in b), suggesting the formation of new structures during thermal annealing;

FIG. 4 is two graphs showing DLS characterization of the assembly of IDPP, M- and ADA-IDPP, where graph a) shows that IDPP does not self-assemble in solution while ADA-IDPP and M-IDPP form micelles with similar $R_h$ at 20° C.<$T_t$, and graph b) shows that unlike IDPP and M-IDPP, the hydrodynamic size of ADA-IDPP irreversibly increases after thermal annealing suggesting a change in the assembly state due to physicochemical properties of ADA. mean±SD (n=3). Two-way Analysis of Variance, ****: p-value <0.0001;

FIG. 5 shows a TEM of ADA-IDPP after thermal annealing, where panel a) shows that ADA-IDPP forms elongated fibers with an average width of 32.9±4.0 nm (n=80), and panel b) shows that BMT-IDPP$_2$ forms bottle-brush structures with noticeably thinner cores, the average width of 7.7±1.6 nm (n=50). mean±SD;

FIG. 6 shows the in silico assembly of M-peptide, and ADA-peptide using all-atom molecular dynamics simulations, where panel a) shows a snapshot of 15 M-peptide molecules showing core-shell structure with myristoyl chains in the core and peptides forming the shell at 40° C., panel b) shows a snapshot of 15 ADA-peptide aggregate with ADA chains and terminal azide on the surface of aggregate along with the peptides at 40° C., and panels c) and d) show the variation in the radius of gyration ($R_g$), and the solvent accessible surface area (SASA) of the M-peptide (black) and ADA-peptide (red) aggregates over 30-60° C.

Figure 9:
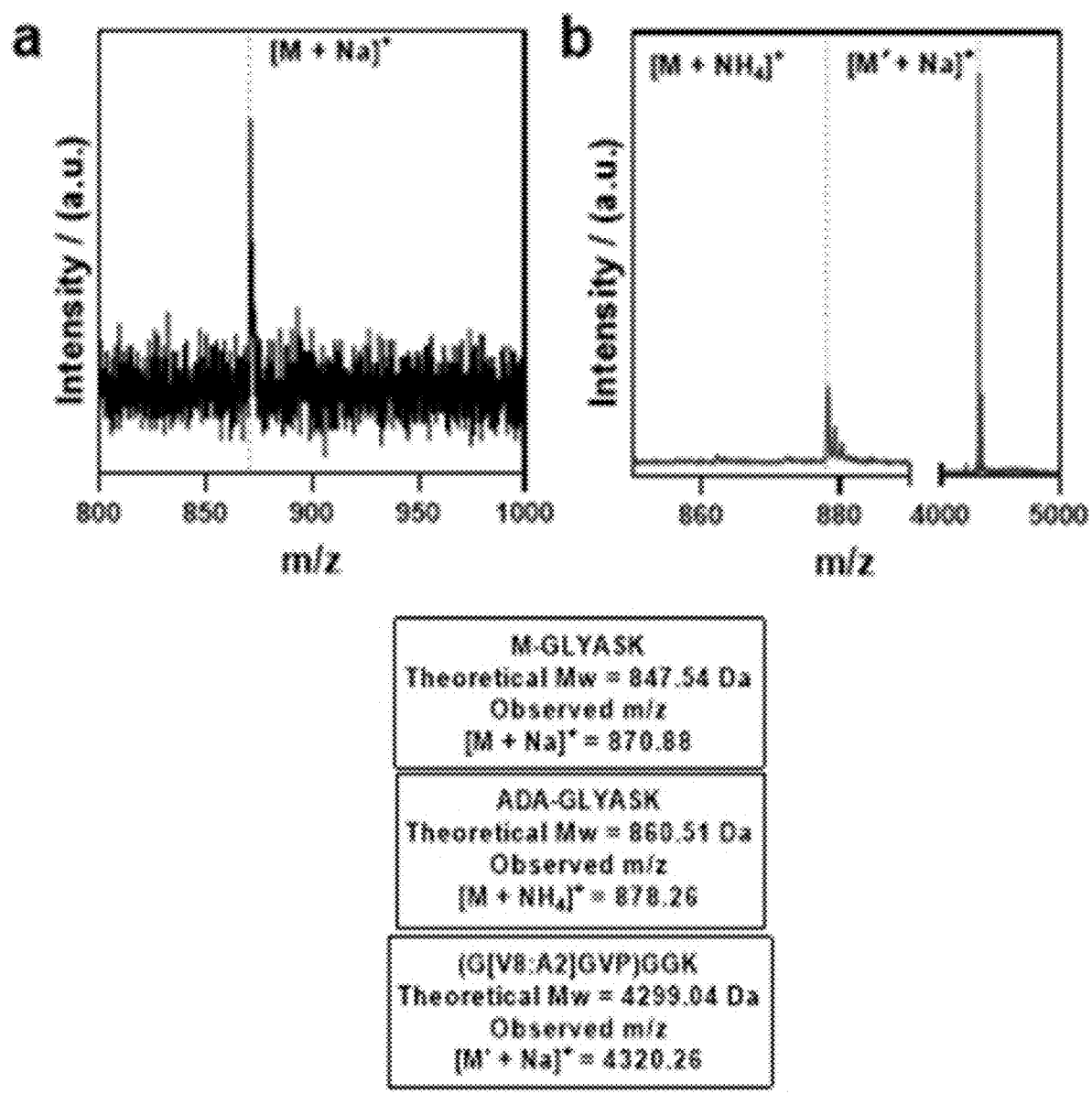
Figure 10:
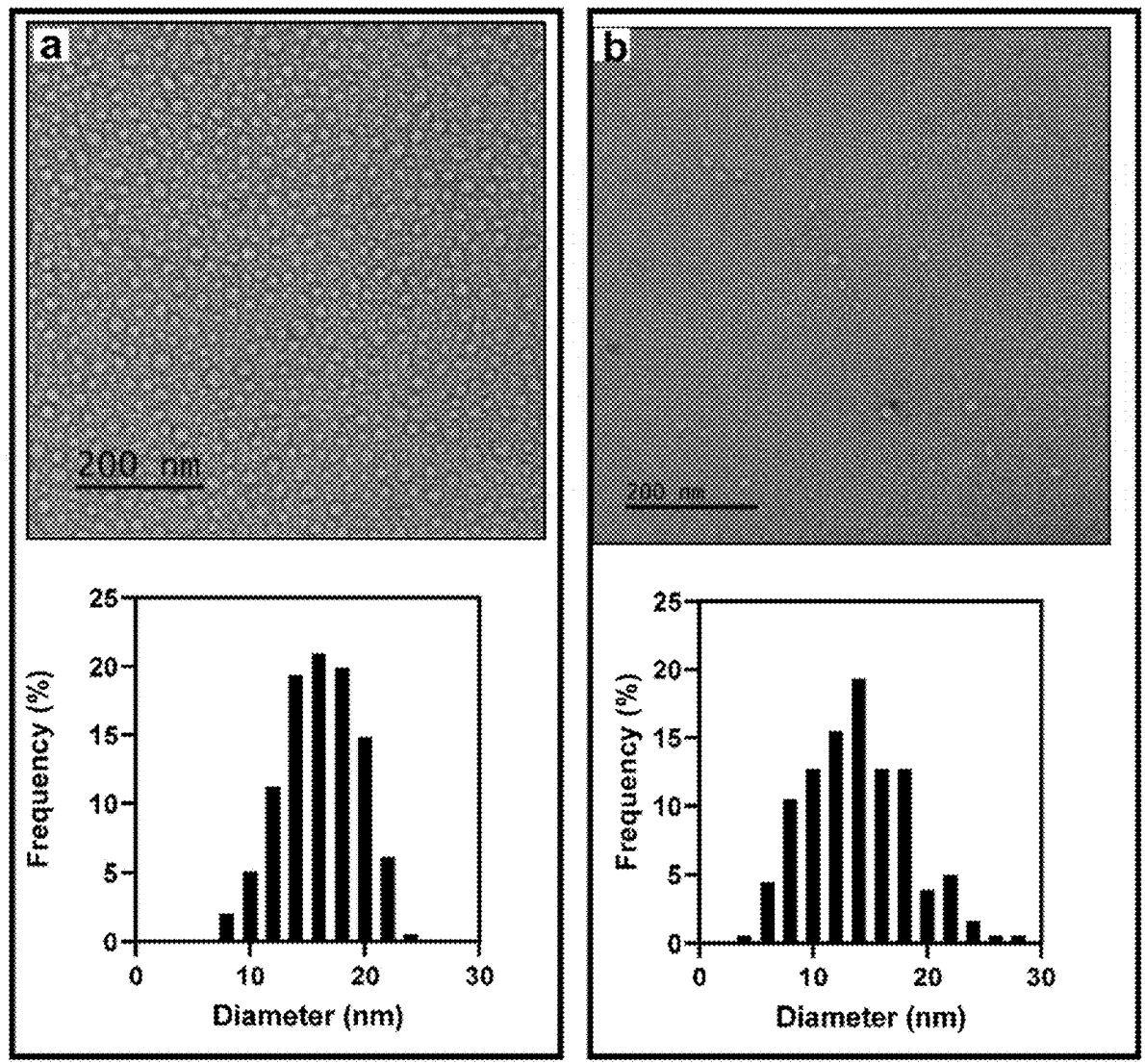
Figure 11:
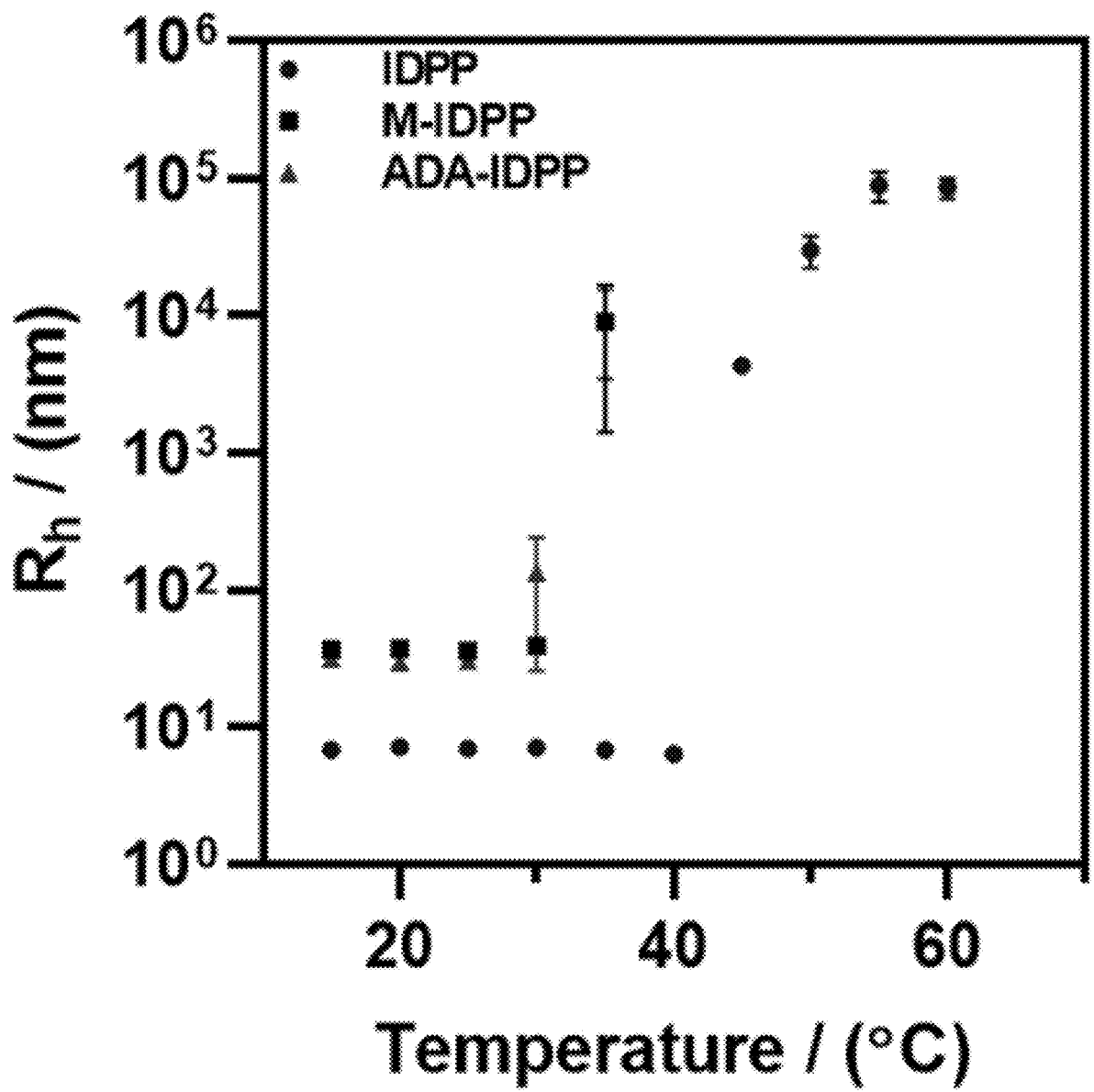
Figure 12:
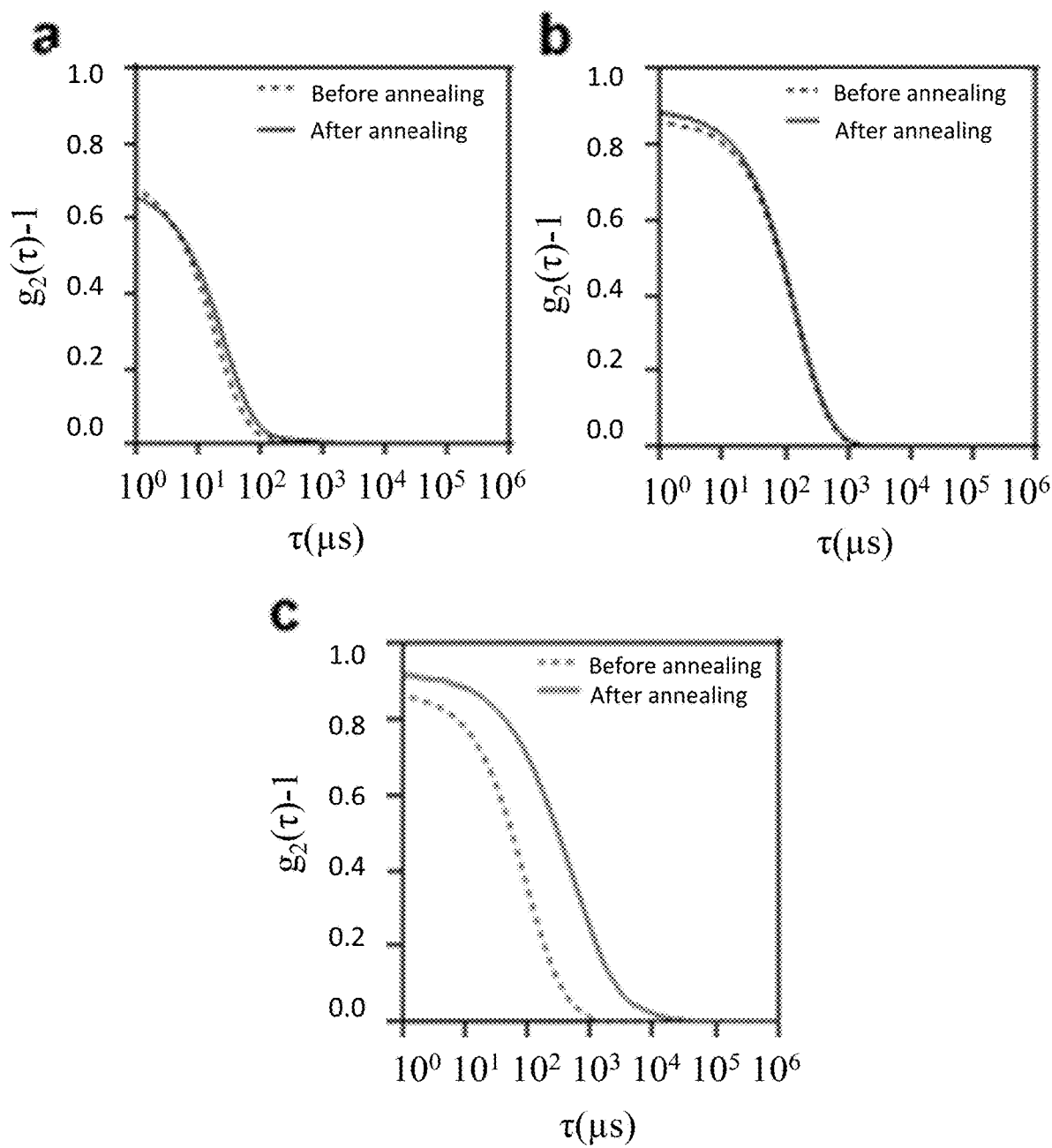
Figure 13:
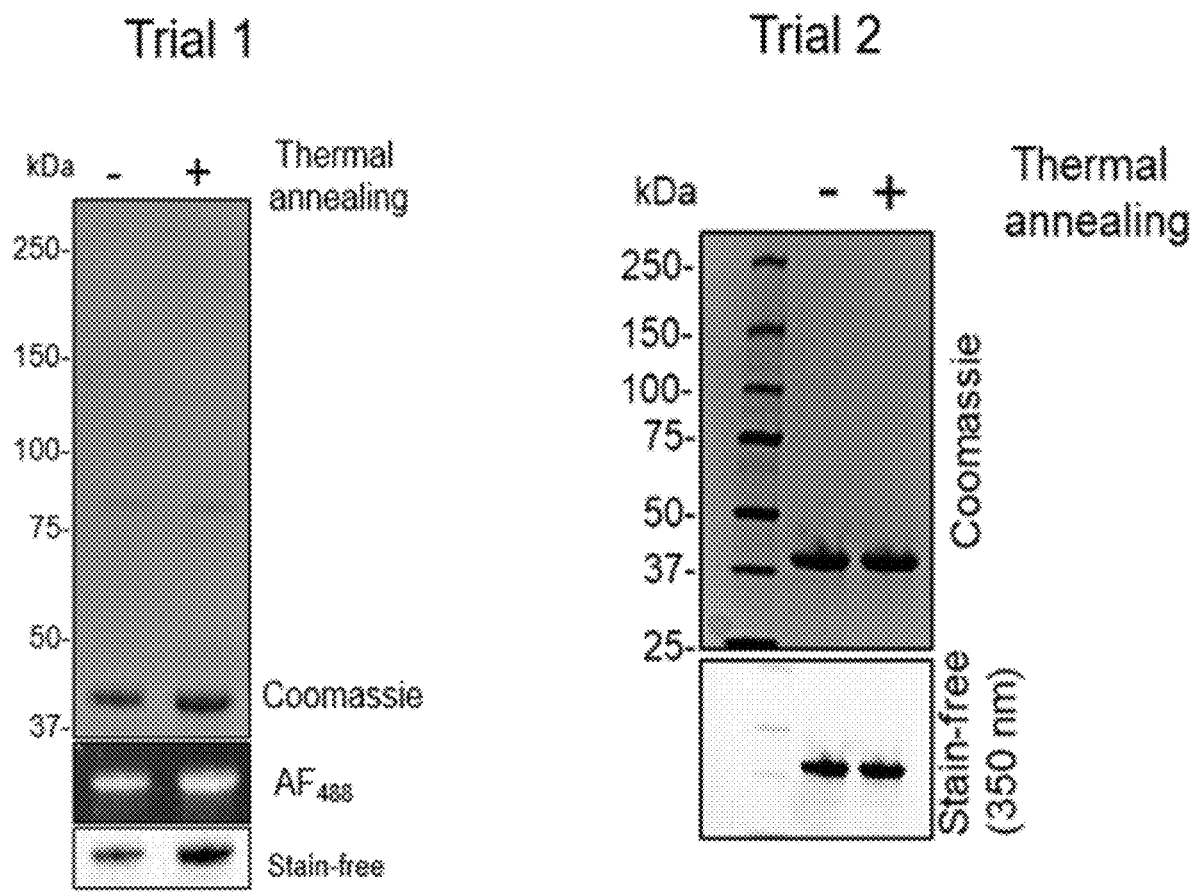
Figure 14A:
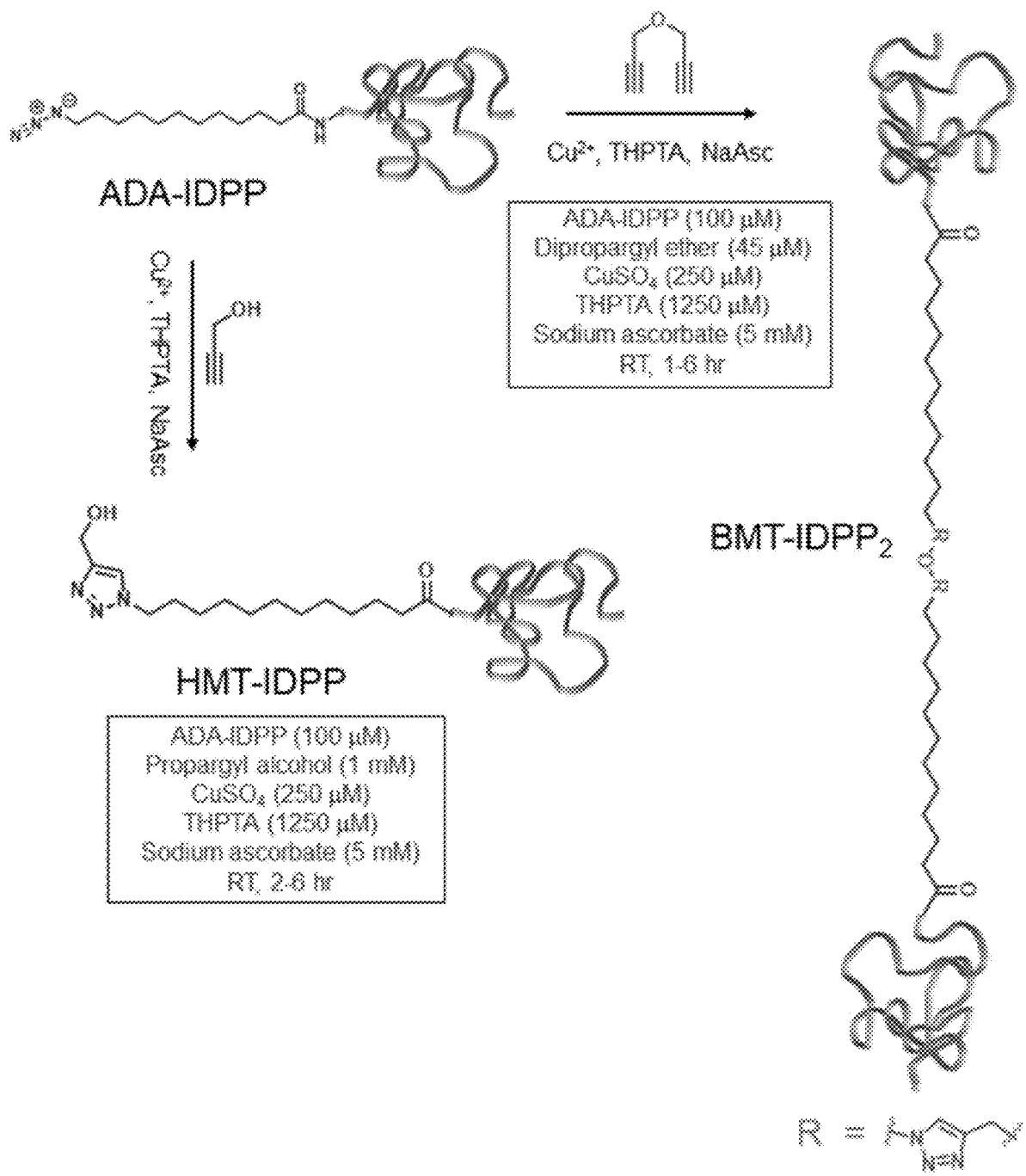

FIG. 9 is a series of graphs of the MALDI-TOF-MS of N-terminal peptide fragment of M-IDPP (a) and ADA-IDPP (b) after digestion with trypsin to confirm the regioselective modification. There are 9 lysines in M-IDPP (and ADA-IDPP), 8 of which are distributed throughout the sequence of IDPP and one is located within the ARF2 recognition sequence. As shown in panel b, the ADA modification was only observed at the N-terminal, supported by the peak at m/z=878.16, which was assigned to the ammonium adduct (present in the trypsin digest buffer). Azides may decompose during the MALDI ionization process and have been found to form metastable ions with the observed m/z differing from the theoretical molecular weight. For ADA-IDPP, none of the of internal lysine residues were modified and only unmodified IDPP fragments were observed (m/z=4320.26). Though MALDI-TOF-MS is not quantitative, this result supports the notion that ADA is not added to the ε-amine of the lysine residues and is instead added to the N-terminal of the ARF2 sequence. Vertical dashed lines denote theoretical molecular weight;

FIG. 10 is a series of TEMs of negatively stained M-IDPP (a) and ADA-IDPP (b) before thermal annealing. M-IDPP forms spherical micelles with an average diameter of 15.3±3.6 nm (N=200); ADA-IDPP forms spherical micelles with an average diameter of 12.8±4.5 nm (N=181). Inset in each panel summarizes the distribution of measured diameters. The observed size of each construct in dried state (TEM) is smaller than the hydrodynamic radius in solution determined by DLS (cumulant method);

FIG. 11 is a graph of DLS characterization of the self-assembly of IDPP, M-IDPP, and ADA-IDPP in solution at different temperatures. The hydrodynamic radius of the constructs remained unchanged below $T_t$, and all three constructs formed large macroscopic (>□m size) polymer-rich coacervates above $T_t$, consistent with the size of polymer-rich coacervates formed by IDPPs.[23] The temperature of the protein solution was increased in 5° C. steps, and the protein solution was incubated at each temperature for 1 min before the start of the DLS measurement. The observed $T_t$ from DLS experiment is in excellent agreement with the $T_t$ observed from the turbidimetry for IDPP, ADA-IDPP, and M-IDPP. The error bars represent standard deviation of three measurements;

FIG. 12 is a series of graphs of the DLS auto-correlation functions of IDPP (a) and M-IDPP (b) and ADA-IDPP (c) before and after thermal annealing (dashed and solid lines);

FIG. 13 shows azide moiety in ADA-IDPP does not decompose during thermal annealing. To ensure that the azide group is still present in the self-assembled fibers after thermal annealing, $AF_{488}$-DBCO was added to ADA-IDPP after heating and cooling the protein solution above and below LCST (thermal cycle: 20° C.→40° C.→20° C.). Dynamic light scattering was used to confirm the formation of larger hysteric aggregates after the completion of the thermal cycle. As a control, a solution of ADA-IDPP before thermal annealing, i.e., stored in PBS at T=20° C.<LCST), was also mixed with the fluorophore. Both control and thermally annealed samples (trial 1, lane 2 and 3) exhibited similar labeling with $AF_{488}$-DBCO dye, consistent with the stability of the terminal azide under the thermal annealing conditions. Additionally, the thermally annealed sample does not contain any higher molecular weight oligomers that are expected form the cross-linking reaction mediated by nitrenes (reactive intermediates formed during azide decomposition).[24] Similar results were observed when the protein solution was heated to 60° C., trial 2, and cooled to 20° C. These two observations support our hypothesis that the aliphatic azide of ADA is thermally stable in the experimental range and does not decompose during the assembly;

FIG. 14A is a schematic of reactions of ADA-IDPP with a telechelic alkyne (dipropargyl ether, green) to convert the single tail amphiphile into a bolaamphiphile (BMT-IDPP$_2$, BMT: bis(methoxy-1,2,3-triazole); and the reaction of ADA-IDPP with propargyl alcohol (purple) to convert azide into functionalized triazole (HMT-IDPP, HMT: hydroxylmethyl-1,2,3-triazole).

Figure 3:
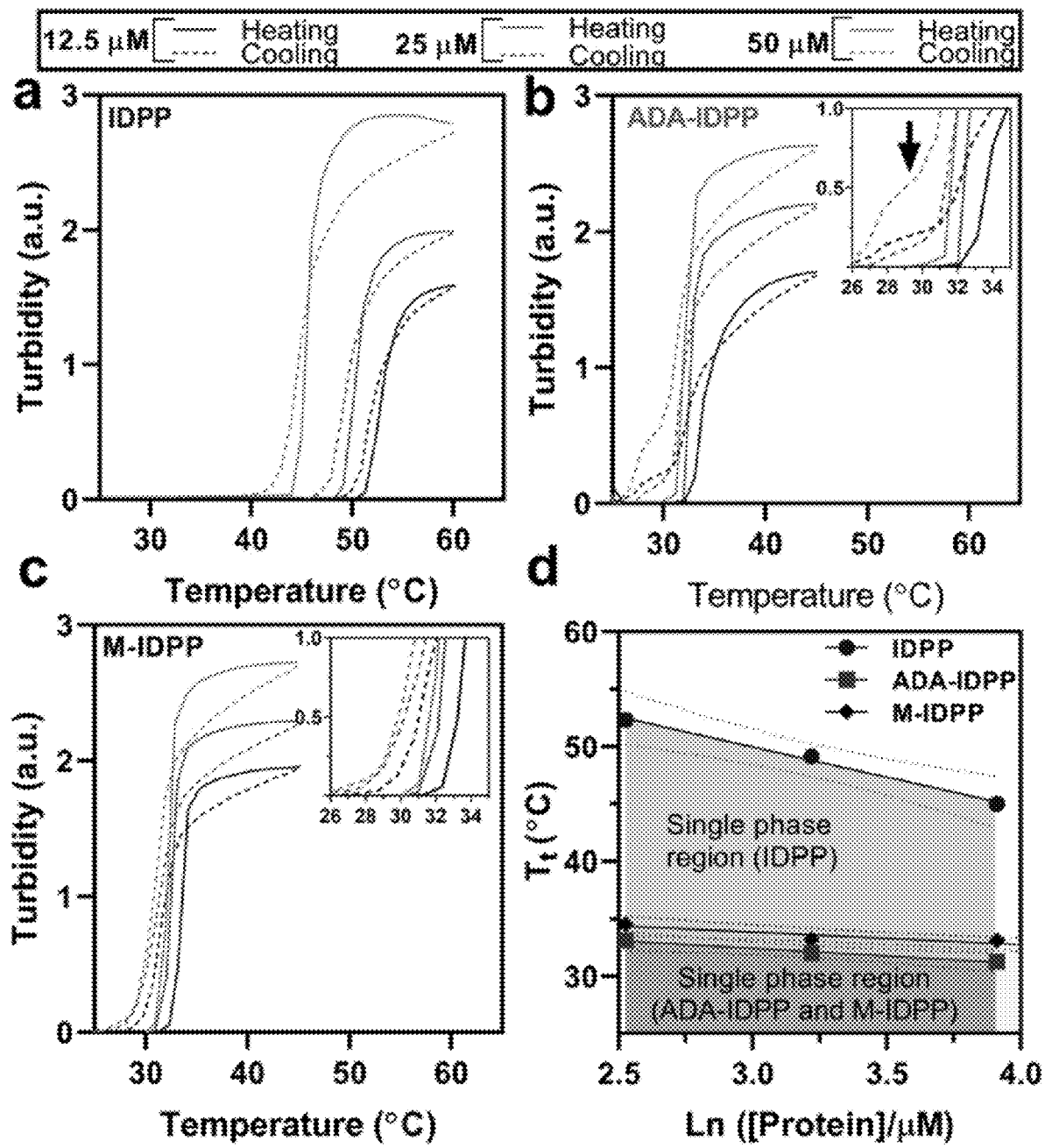
Figure 5:
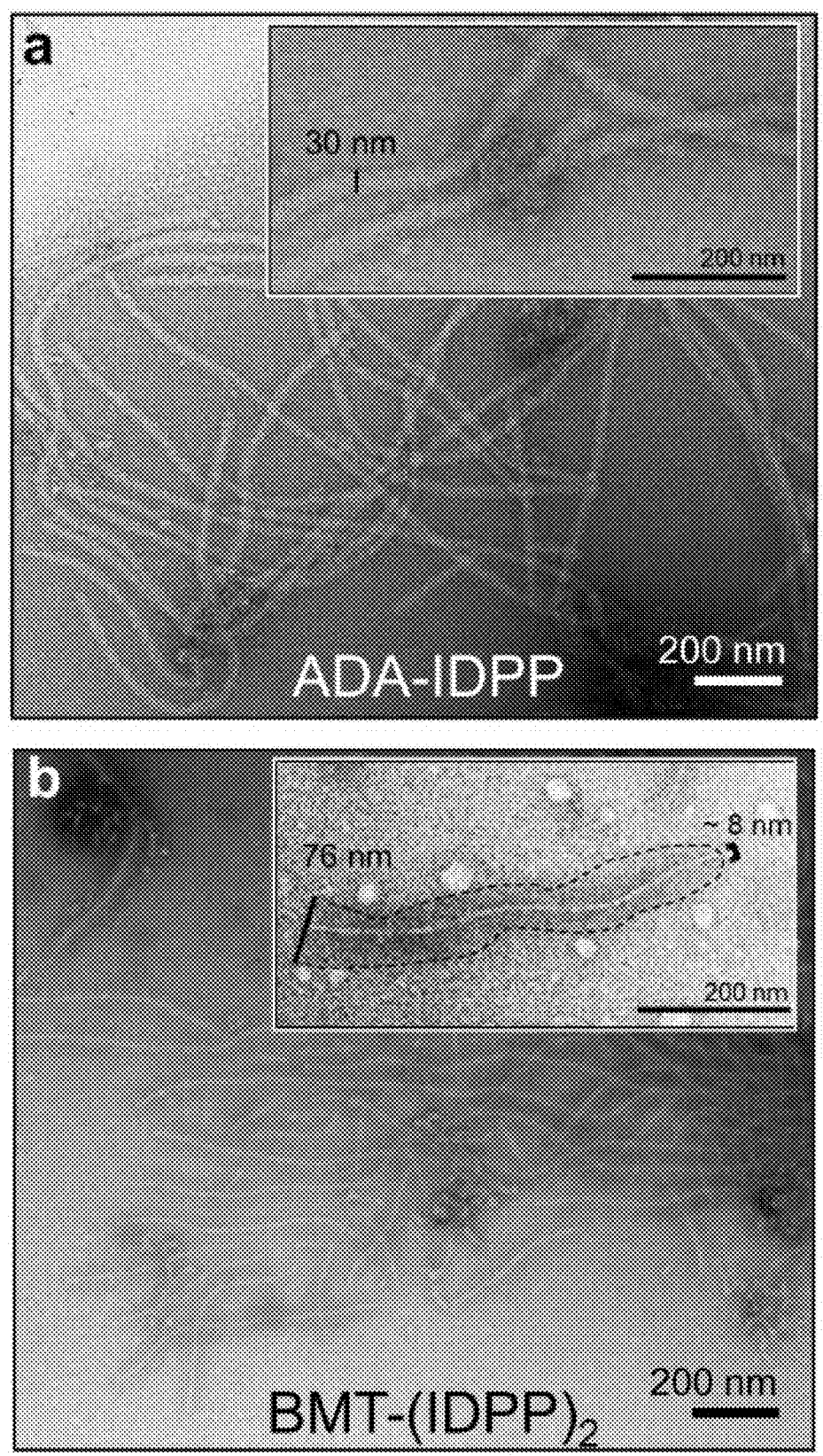
Figures 14B, 14C:
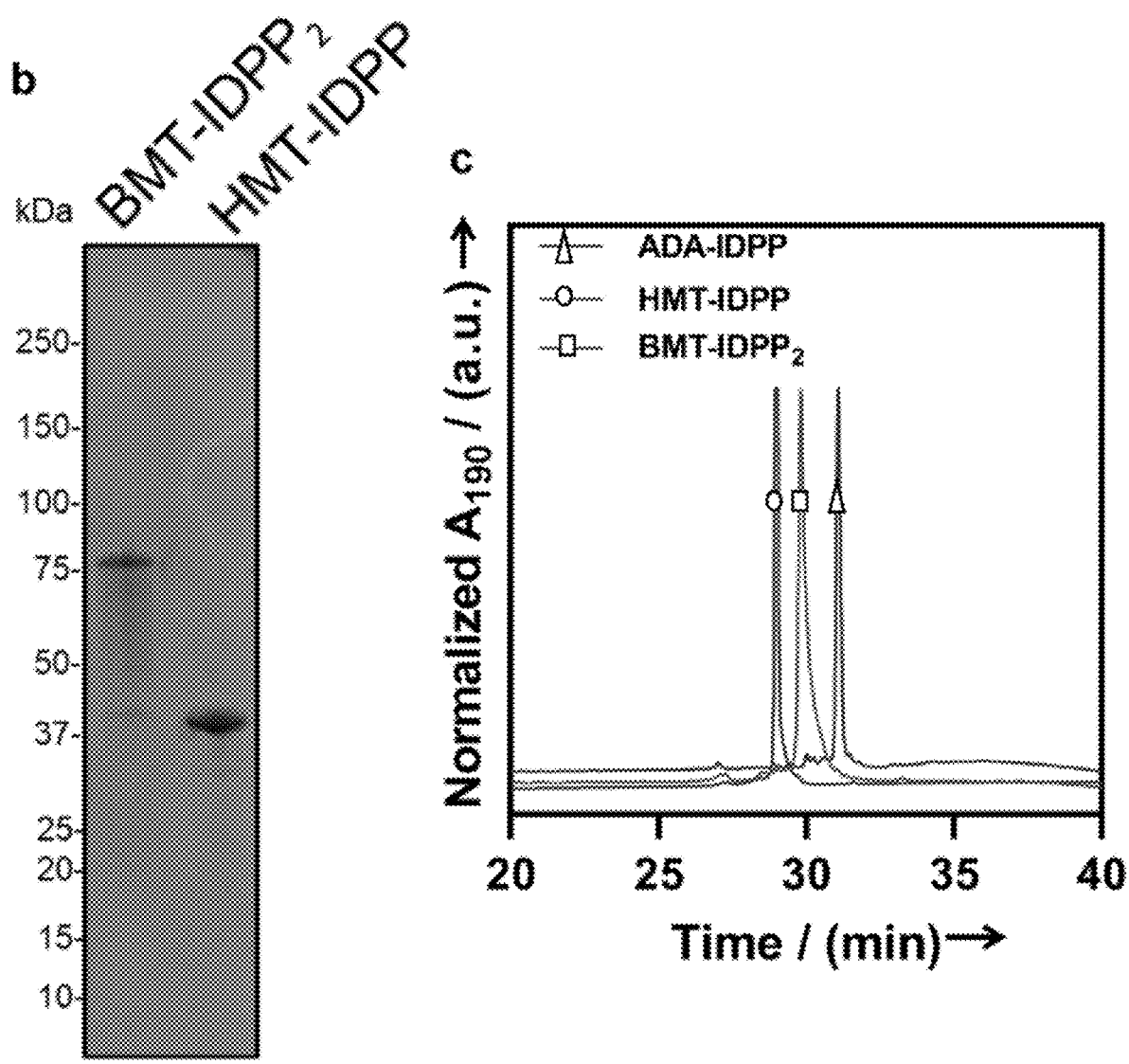
Figure 15:
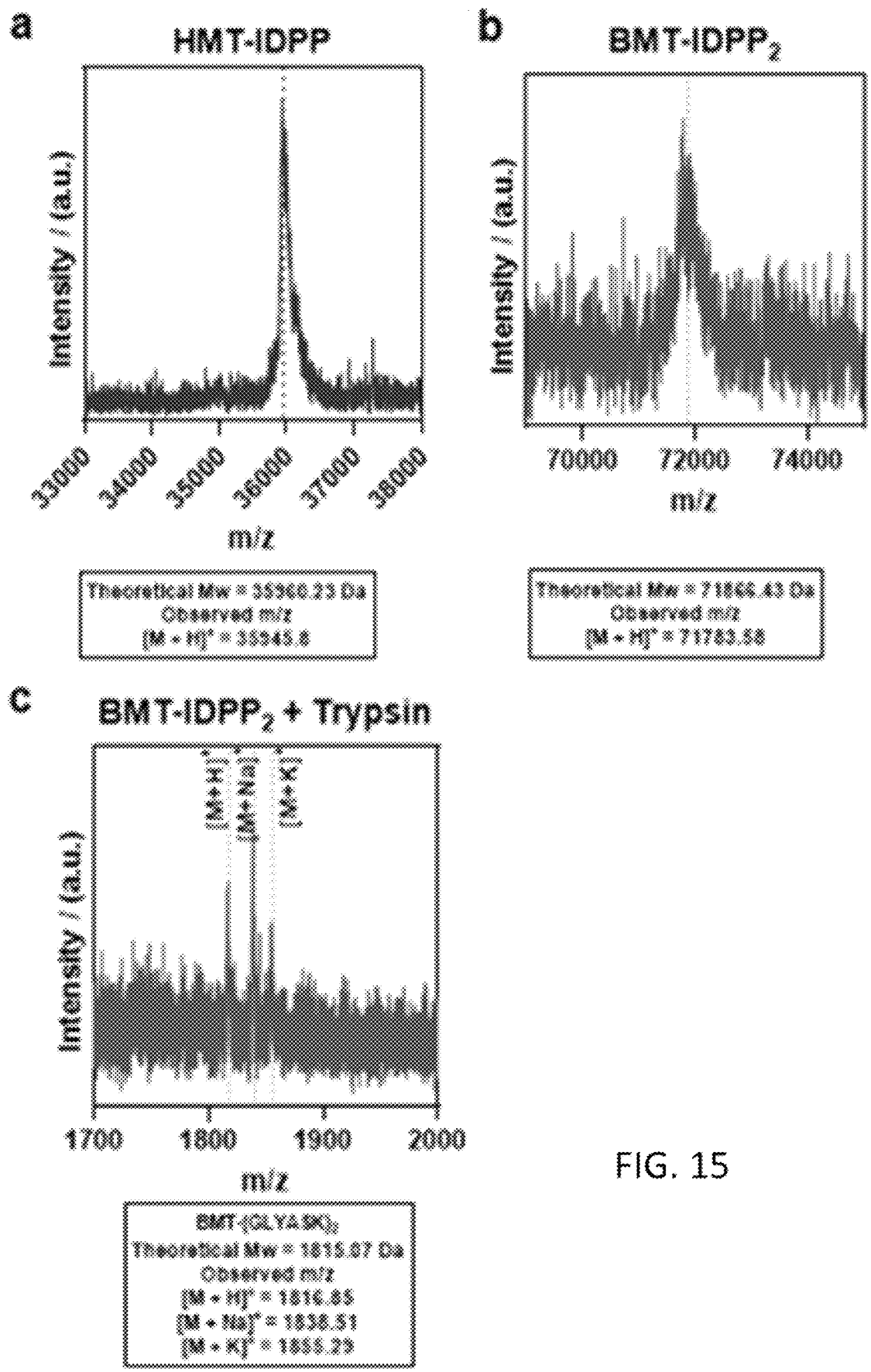
Figure 16:
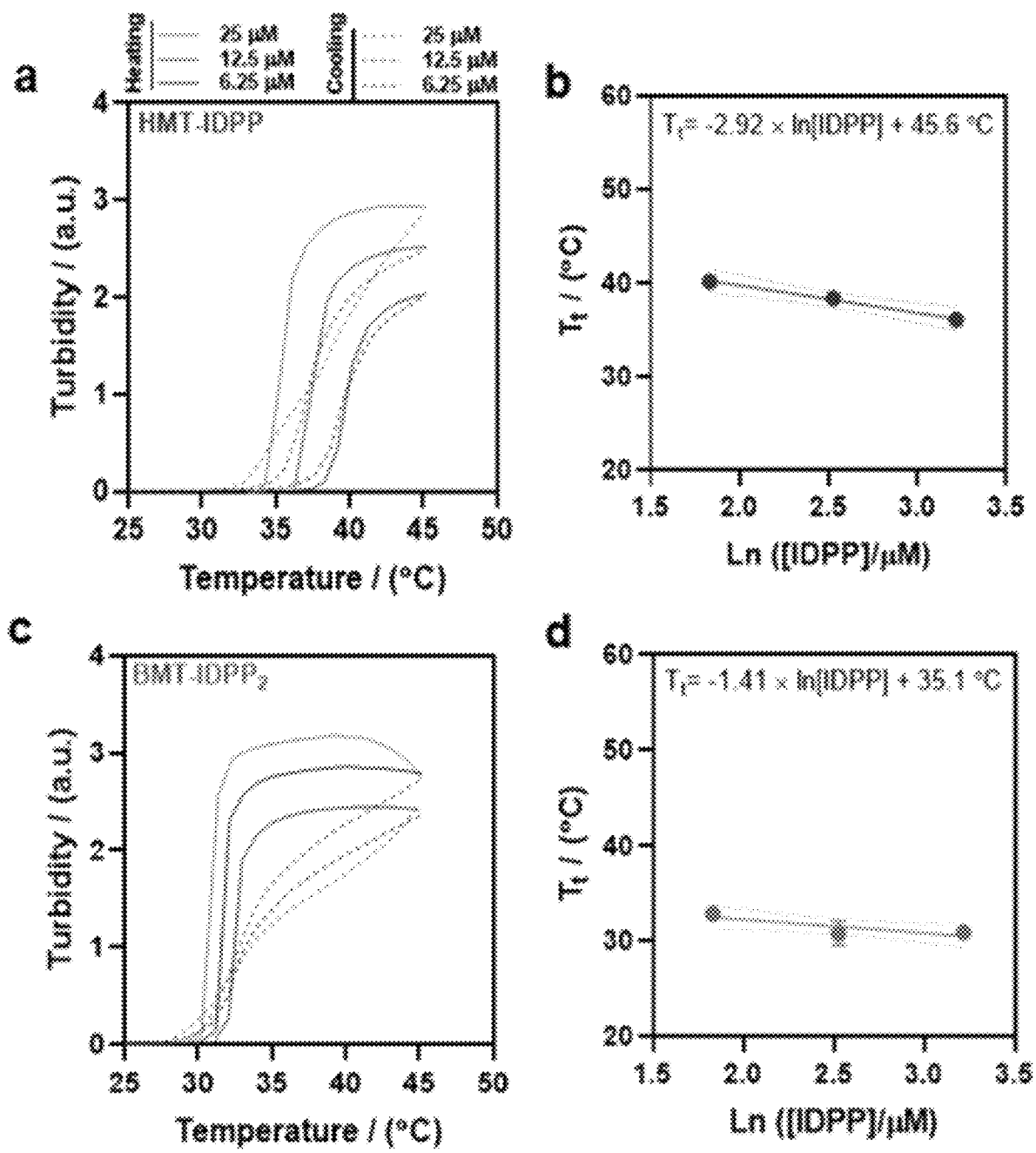
Figure 17:
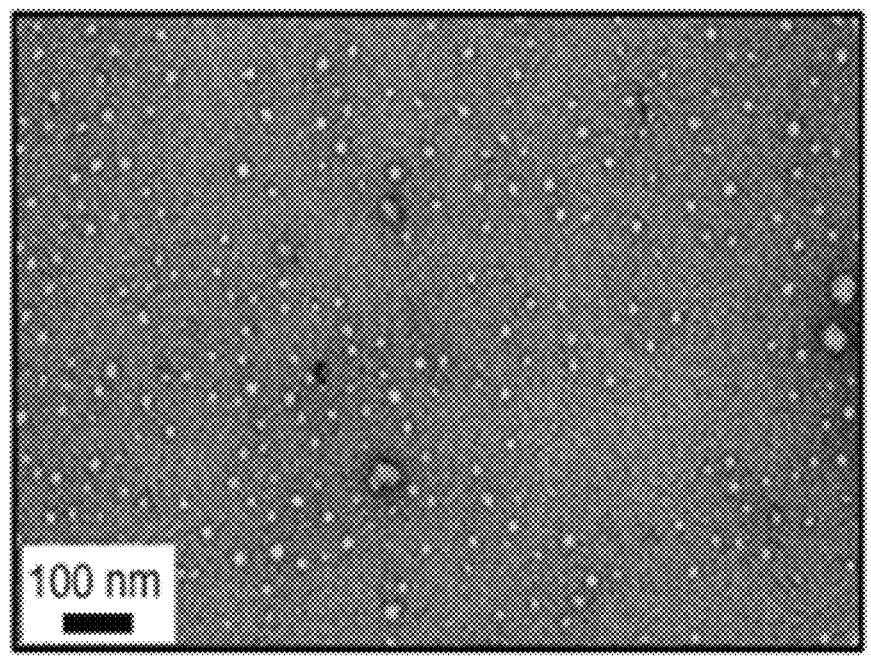
Figure 17:
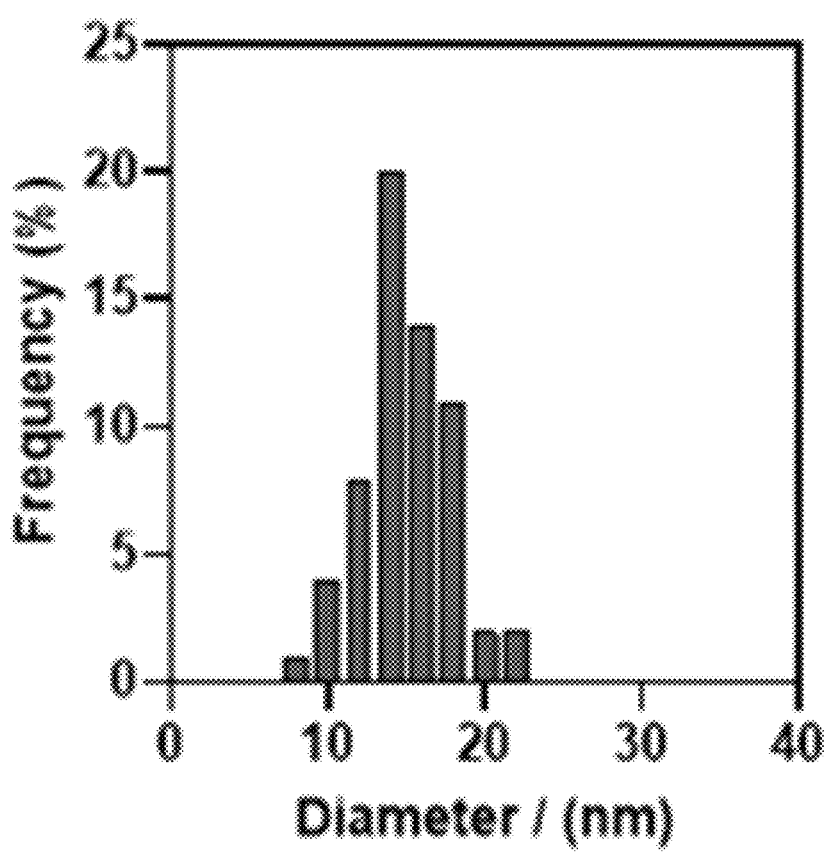
Figure 18:
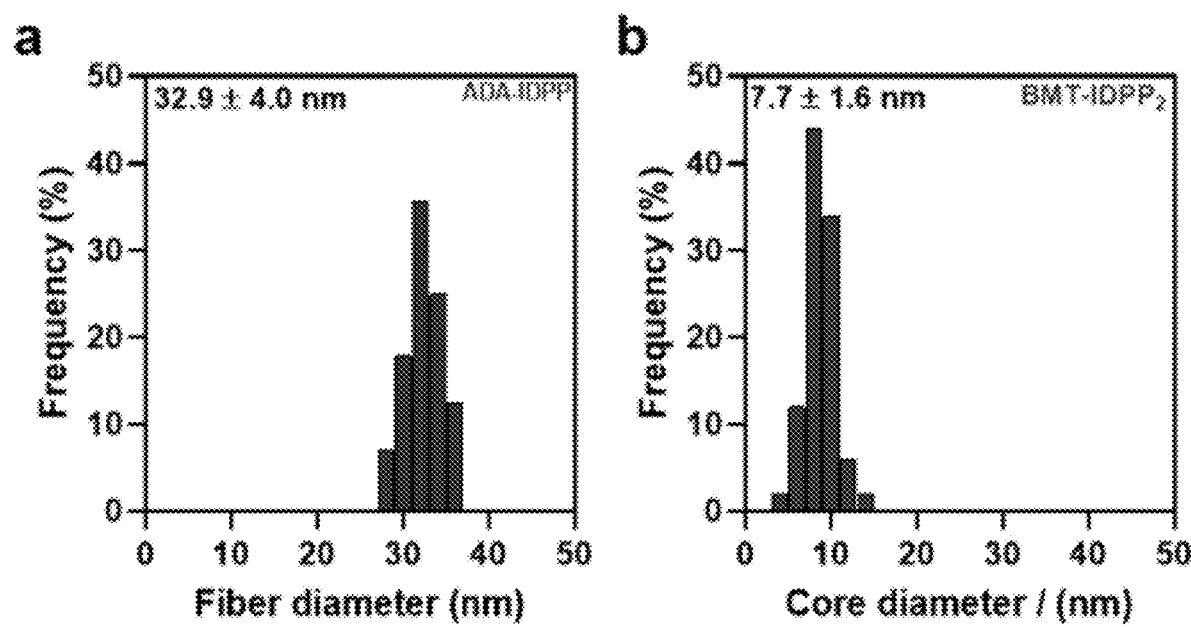
Figure 19:
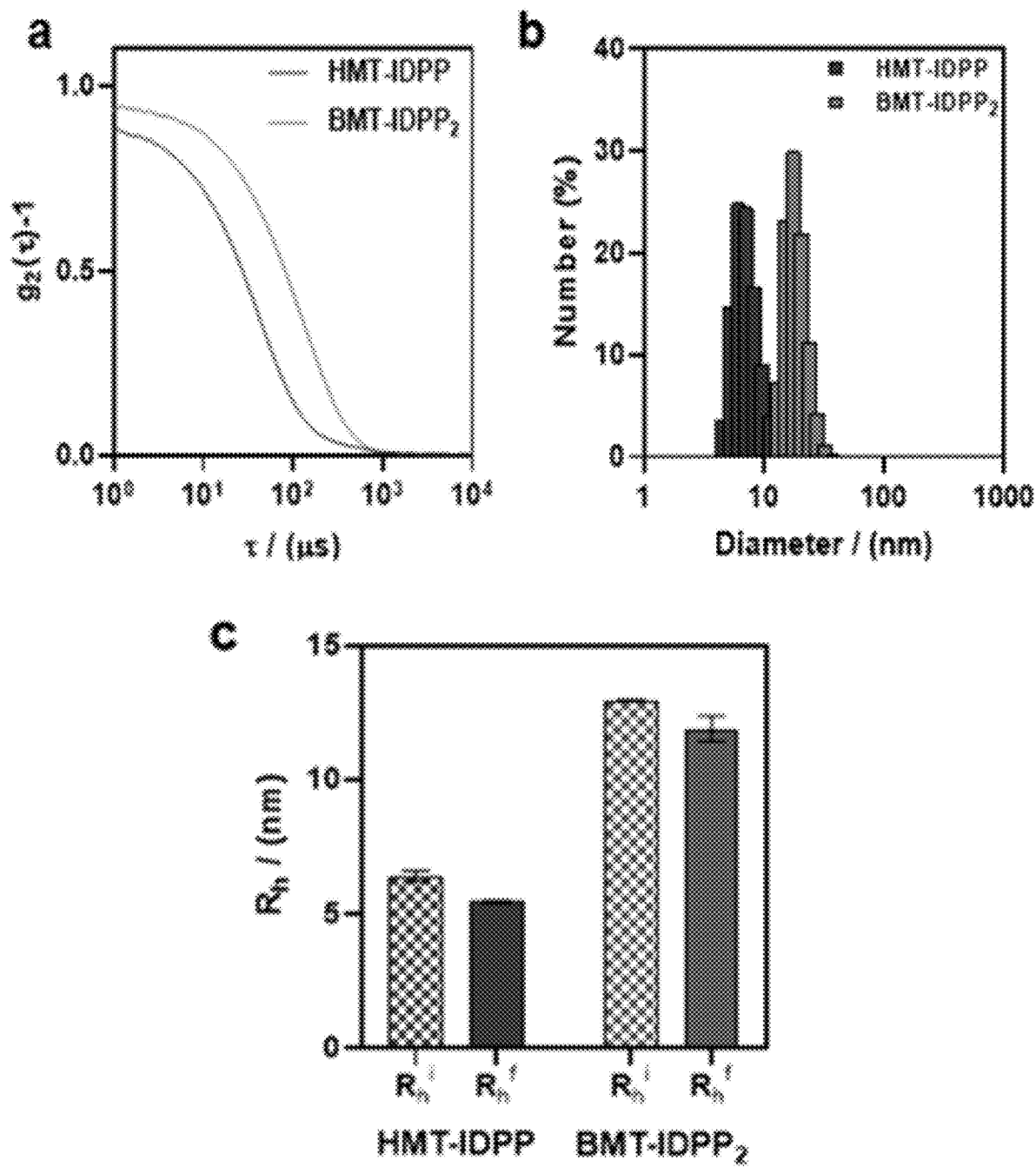
Figure 20:
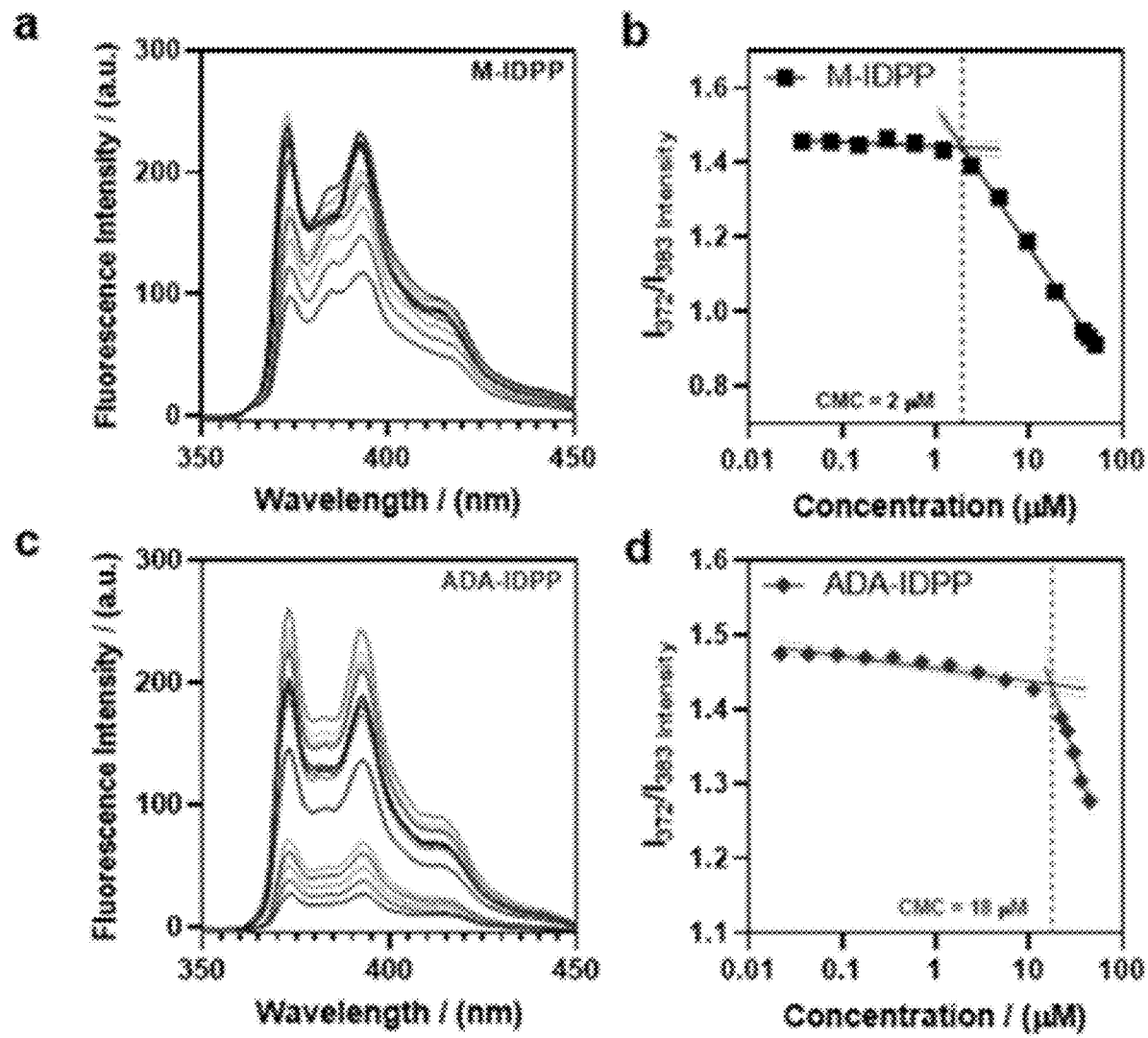
Figure 21:
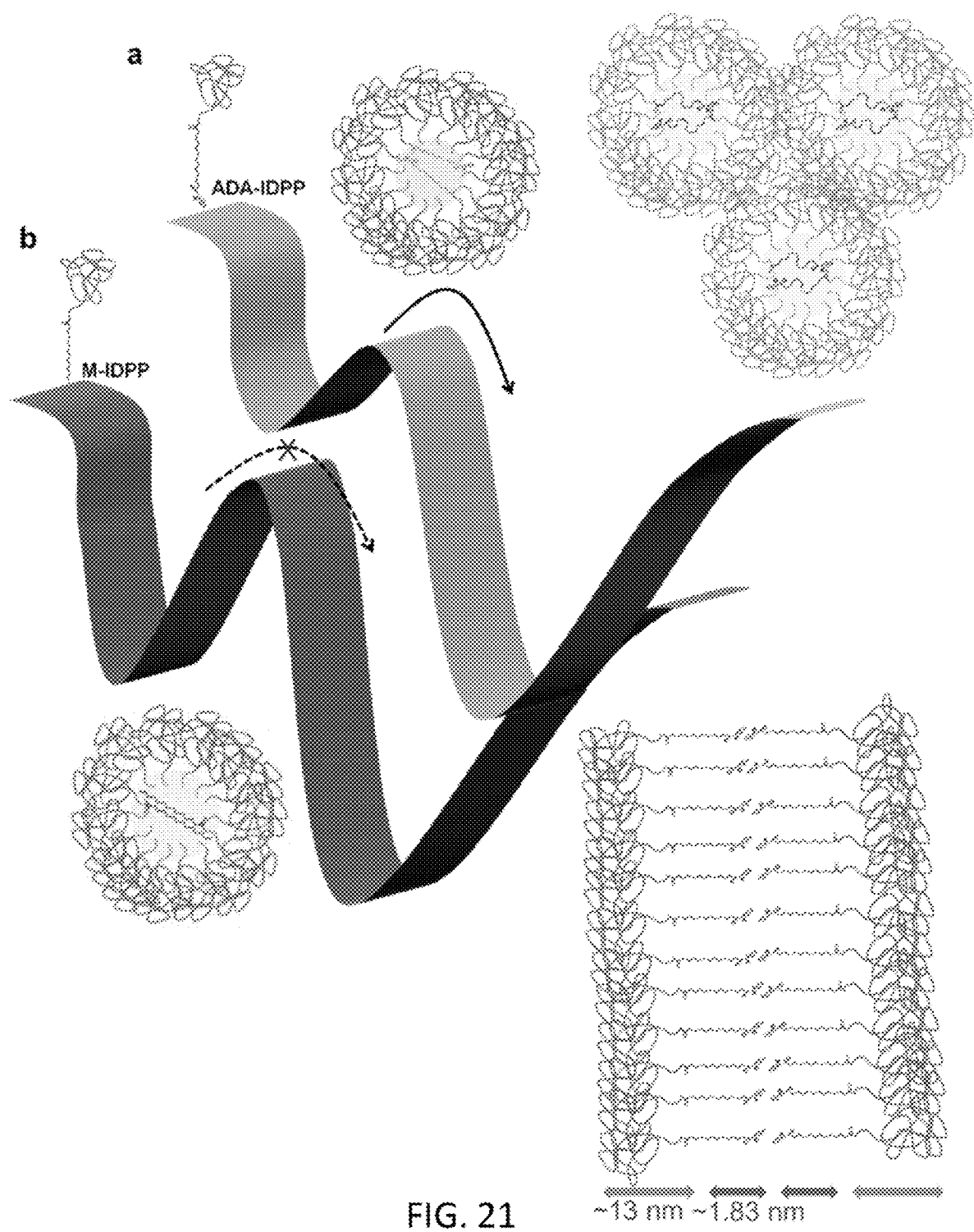

FIGS. 14B and 14C is a series of panels showing that copper assisted alkyne azide cycloaddition (CuAAC) can be used to functionalize the w-azide moiety of the non-canonical lipoprotein, where Panel b is an SDS-PAGE analysis of purified BMT-IDPP$_2$ and HMT-IDPP and Panel c is an RP-HPLC chromatogram of ADA-IDPP, HMT-IDPP, BMT-IDPP$_2$ using a gradient of water and acetonitrile on a C18 column. The retention time of each construct is inversely correlated to the polarity of the lipid chain end;

FIG. 15 is a series of graphs of the MALDI-TOF-MS of HMT-IDPP (a) and BMT-IDPP$_2$ (b). MALDI-TOF-MS of N-terminal peptide fragment of BMT-IDPP$_2$ digested with trypsin (c). Vertical dashed lines denote theoretical molecular weight;

FIG. 16 is a series of graphs of temperature-programmed turbidimetry that was used to monitor the LCST phase-transition of HMT-IDPP (a,b) and BMT-IDPP$_2$ (c,d). Both HMT-IDPP and BMT-IDPP$_2$ exhibits reversible LCST phase behavior. Since the concentration of IDPP influences the LCST, the concentration of the IDPP domain was chosen instead of the nominal concentration of each (i.e., [HMT-IDPP]=[IDPP]; 2×[BMT-IDPP2]=[IDPP]). The phase-diagram of HMT-IDPP (b) and BMT-IDPP$_2$ (d), showing the boundaries between the single phase (below each line) and the two-phase region (above each line). Both lipoproteins exhibited lower transition temperatures compared to unmodified IDPP at identical concentrations (FIG. 3a). However, the concentration dependence of $T_t$ was different for each construct. The dashed lines represent the 90% confidence interval of the line fitted to the experimentally observed transition temperatures, see the summary of derived parameters in Table 3;

FIG. 17 is a TEM of BMT-IDPP$_2$ below LCST which forms spherical aggregates with an average diameter of 14.1±3.0 (N=62), and the distribution of measured diameters;

FIG. 18 is a series of graphs of (a) The distribution of measured diameter of fibers formed by ADA-IDPP after thermal annealing (N=80), corresponding to FIG. 5a,b. Graph (b) shows the distribution of core diameters in bottlebrush structures formed by BMT-IDPP2 (N=50), corresponding to FIG. 5c,d;

FIG. 19 is a series of graphs showing (a) the DLS auto-correlation functions of HMT-IDPP and BMT-IDPP$_2$ below LCST. Graph (b) shows the number-size distributions of HMT-IDPP and BMT-IDPP$_2$. HMT-IDPP does not self-assemble as it formed small particles with an average (peak mean) diameter of 7.3±0.5 (which is consistent with the size of unassembled IDPP with comparable size 5.2 nm). BMT-IDPP$_2$, on the other hand, formed nanostructures with an average (peak mean) diameters of 13.2±0.4 nm, which is significantly larger than the expected hydrodynamic radii of a coiled polypeptide with this length, i.e., for IDPP-IDPP, Rh=~7.4 nm). Graph (c) shows the cumulants analysis (hydrodynamic radius) of the size of HMT-IDPP and BMT-IDPP$_2$ before and after thermal annealing (checkered versus solid fill). No irreversible increase in the size of the aggregates is observed for these two constructs, consistent with the reversible LCST phase-transition observed in the turbidimetry seen in FIG. 18;

FIG. 20 is a series of graphs showing pyrene fluorescence assay to determine the CMC of M-IDPP (a,b) and ADA-IDP (c,d). Raw fluorescence data is plotted in (a) and (c). Calculated peak 1 to peak 3 absorbance ratios for pyrene fluorescence are plotted against M-IDPP and ADA-IDPP concentrations, made in serial dilutions. The calculated CAC is shown as a dashed, vertical line for M-IDPP (a) and ADA-IDPP (d);

FIG. 21 is a schematic of a proposed mechanism to explain the unique temperature-triggered self-assembly observed by ADA-IDPP. Schematic a) shows that ADA-IDPP forms micelles below the LCST but the cores of these micelles are more dynamic than the M-IDPP micelles due to the lower melting point of the ADA. Heating of the sample above the LCST and T$_m$ of ADA can lead to partial melting of the core and rearrangement of the lipoproteins into fibers after thermal annealing. Schematic b) shows that M-IDPP micelles form coacervates above the LCST but the rearrangement of the lipoprotein from micelles to other nanostructures is hindered due to the stability of the micellar core. Once the temperature is lowered below T$_t$, the coacervates will dissolve to form the original micelles.

DETAILED DESCRIPTION OF THE INVENTION

Figure 1:
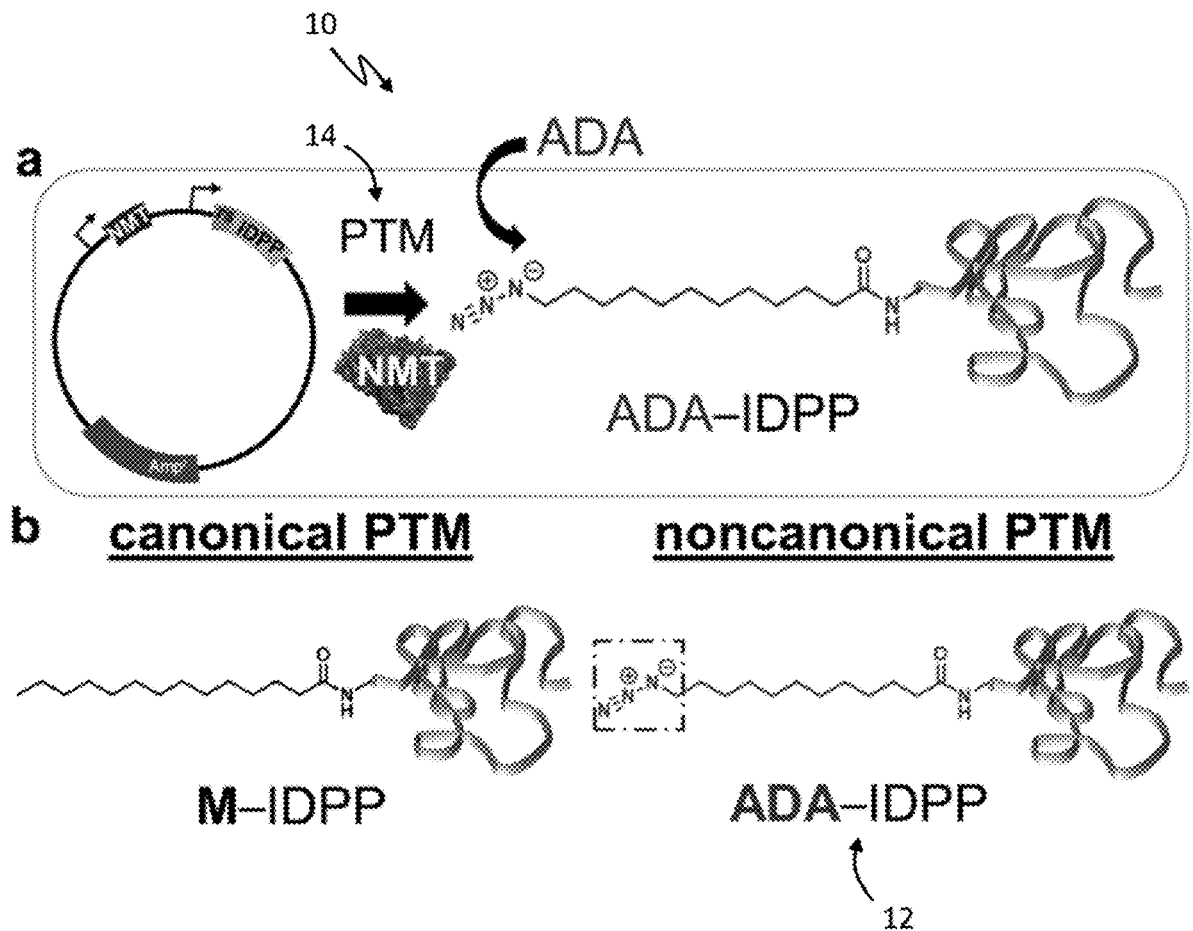

Referring to the figures, wherein like numeral refer to like parts throughout, there is seen in FIG. 1 an approach 10 for synthesizing non-canonical lipoproteins 12 using the substrate promiscuity of the post translational modification (PTM) machinery 14 to modify proteins with artificial lipids to form lipoproteins bearing a non-canonical PTM (ncPTM). Non-canonical lipoproteins are formed from a unique assembly that is absent from natural analogues, due to the different physicochemical properties of artificial and canonical lipids. Additionally, artificial lipids bearing bio-orthogonal groups (e.g., azide) can be derivatized to form complex hybrid materials. The increased hydrophobicity of these artificial lipids distinguishes their utility from non-canonical amino acids with bioorthogonal side chains, as these lipids can be used to simultaneously couple macromolecules and encode a precise and programmable pattern of amphiphilicity. The artificial lipid may comprise any non-natural fatty acid, such as 12-azidododecanoic acid, or any of the at least 100 unnatural substrates of the enzyme (NMT) that are documented in the literature. Generally, compounds with the general formula of R—COOH, in which R contains a linear chain of 12-15 atoms of C, N, O, or S may be a substrate of the enzyme. The only requirement for the lipid is that is contains COOH (carboxylic acid) and its activated form (lipid-CoA) is accepted by the enzyme (NMT or its mutants) as the substrate. This has been demonstrated with azide (ADA) and likely with alkynes. The present invention allows these unnatural lipids to form protein-based nanoparticles.

The ability of N-myristoyltransferase (NMT) to accept analogues of myristic acid, such as 12-azidododecanoic acid (ADA), was used. ADA has been used to profile myristoylated proteins, but the potential of w-azido fatty acid to develop recombinant nanomaterials with controlled hierarchical assembly is virtually unexplored. The present invention co-expressed i) *S. cerevisiae* NMT with ii) an IDPP fused to a peptide substrate of NMT in *E. coli*, as seen in FIG. 1A. The N-terminal glycine of the peptide substrate (GLYASKLFSNL)(SEQ. ID NO: 1) is the site of lipidation. By adding either myristic acid (M) or ADA to media, canonical (M-IDPP) or non-canonical (ADA-IDPP) lipoproteins were obtained. The concentration of ADA and expression time were adjusted empirically to avoid the misincorporation of endogenous myristic acid (See supplementary information for details). M- and ADA-IDPP only differ in the terminal region of each lipid tail, n-propyl vs. N$_3$, as seen in FIG. 1B. Compared to M, the azide group increases the polarity of ADA but reduces its packing-efficiency. These differences in physicochemical properties of the lipid tail should lead to divergent assembly pathways for the M-IDPP and ADA-IDPP.

Figure 2:
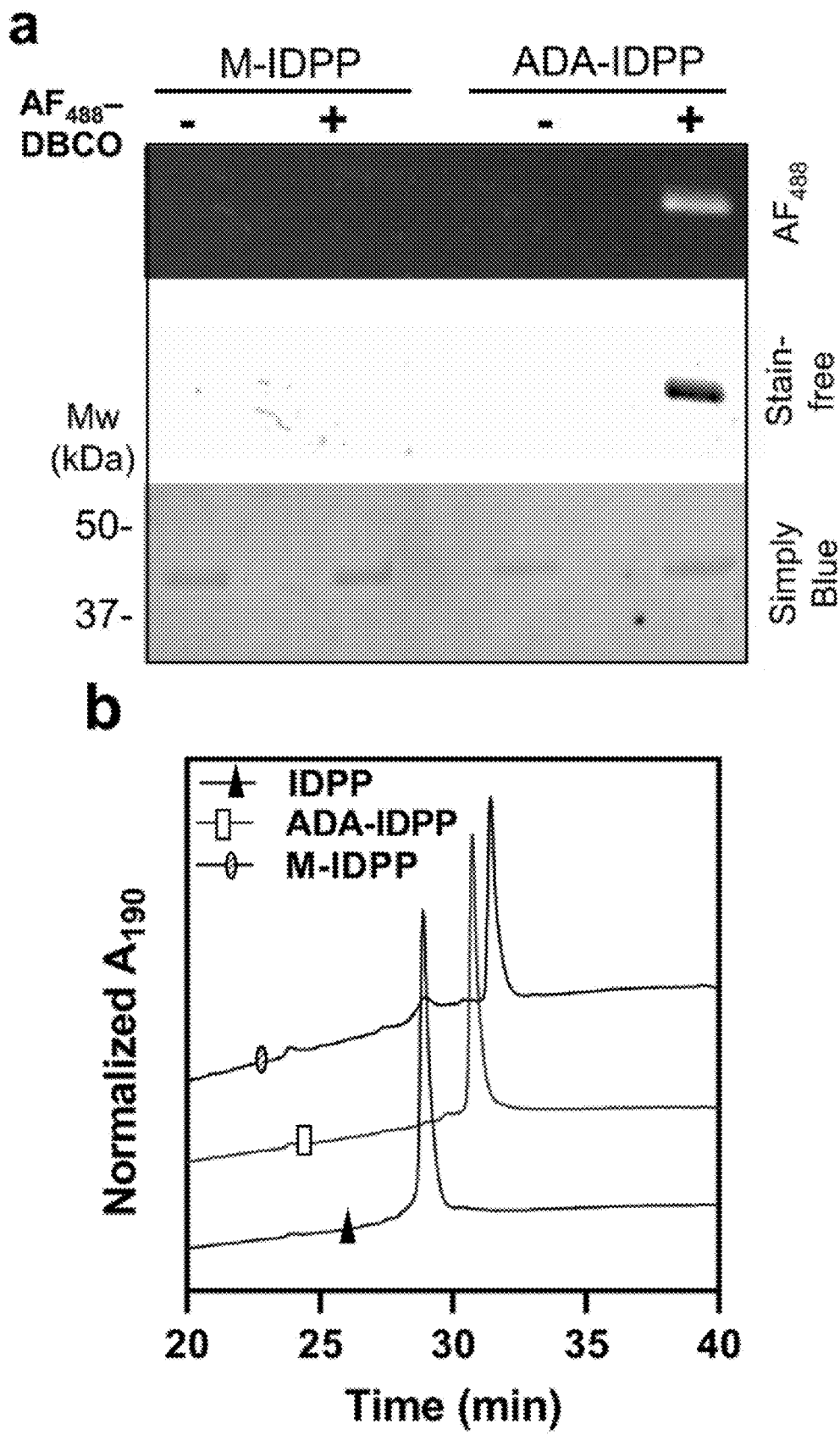

IDPP was derived from the consensus sequence of tropoelastin, (GXGVP)$_{80}$ containing a mixture of valine and alanine (8:2) in X position. IDPPs derived from elastin exhibit lower critical solubility temperature (LCST) phase behaviour and have been used in numerous biomedical and materials science applications. This LCST phase behavior was used to purify IDPP (negative control), M-IDPP, and ADA-IDPP using inverse transition cycling (ITC) after expression (yield of purified proteins=3-10 mg/L of culture). Mass spectrometry (FIG. 10-1) and labelling with AF$_{488}$-DBCO, as seen in FIG. 2A, confirmed that ADA was efficiently and site-specifically incorporated into desired polypeptides and that the azide group remained stable after ITC.

Reverse-phase HPLC was used to quantify the hydrophobicity of each construct by comparing their retention time (t$_R$). As shown in FIG. 2B, the observed trend—t$_R$ (min)= IDPP (28.8)<ADA-IDPP (30.7)<M-IDPP (31.5)—is consistent with the increased hydrophobicity of M-IDPP compared to ADA-IDPP.

Modification with ADA was investigated to determine whether it modulates the liquid-liquid phase separation of IDPP. The turbidity of solutions of IDPP, ADA-IDPP, and M-IDPP, seen in FIGS. 3A through 3C) was monitored while heating or cooling the sample at a rate of 1° C./min. The LCST phase transition resulted in a sharp increase in the turbidity of the solution when the temperature was increased above the transition temperature ($T_t$). As shown in the partial temperature-composition phase diagram, see FIG. 3D and Table 3, both canonical and non-canonical lipids modulated the phase boundaries of parent IDPP. M- and ADA-IDPP exhibited lower $T_t$ compared to the IDPP, and ~75% reduction in the slope of phase-boundaries defined by $T_t$ versus the natural log of the concentration. The observed pseudoplateau is a possible indicator of the self-assembly of M- and ADA-IDPP at this concentration range. Intriguingly, a closer inspection of the cooling curves revealed a difference in the reversibility of phase transition between the constructs. While the cooling curve of IDPP and M-IDPP, closely matched the heating curve (i.e., smooth change in turbidity), a noticeable shoulder was observed in the cooling curves of ADA-IDPP (at 27-29° C., marked with an arrow in the FIG. 3B inset). Though no macroscopic aggregates were observed in the cuvettes, it was hypothesized that this unexpected behaviour may point to the formation of a new self-assembled structure unique to ADA-IDPP after thermal annealing.

Figure 4:
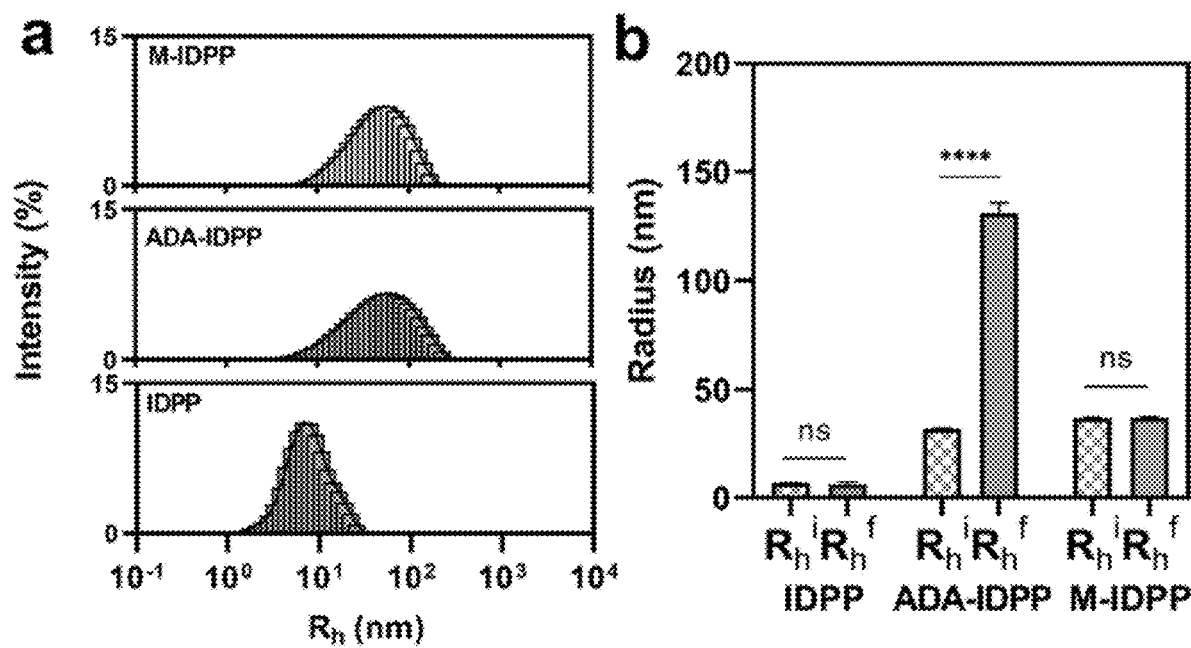

Dynamic light scattering (DLS) and Transmission electron microscopy (TEM) were used to test the hypothesis derived from the turbidimetry. Below $T_t$, IDPP did not self-assemble, as seen in FIG. 4A, as the hydrodynamic radius ($R_h$=6.8±0.2 nm) matched the expected size for the unimer of a coiled protein. The increased $R_h$ of M-IDPP (36.9±0.2 nm) and ADA-IDPP (31.9±0.3 nm) confirms the self-assembly of these constructs, as seen in FIG. 4A. TEM confirmed that M-IDPP (FIG. 10a) and ADA-IDPP (FIG. 10b) form similar spherical micelles below $T_t$, thus conclusively proving that ncPTM can drive the assembly of the recombinant lipoprotein into micelles despite significant differences in the hydrophobicity of the lipid tails ($\Delta$ log $P_{ADA-M}$=0.4).

The hydrodynamic size remained unchanged below the $T_t$ of each construct (FIG. 11). Above LCST, DLS indicated the formation of large (>μm size) polymer-rich coacervates. When the temperature was lowered to 20° C. (below $T_t$), to mimic the effect of thermal annealing, only ADA-IDPP exhibited non-equilibrium (hysteretic) increase in the hydrodynamic size while the size of IDPP and M-IDPP were indistinguishable before and after thermal annealing, as seen in FIGS. 4B and 12). This data indicates that the pathway-dependent differences in the phase behaviour of two lipoproteins originate from the changes in the size or morphology of ADA-IDPP assemblies after thermal annealing. The decomposition of ADA was also ruled out as the cause of the hysteresis, as the aliphatic azide remained accessible to synthetic elaboration after thermal annealing (FIG. 13).

TEM confirmed that after thermal annealing, ADA-IDPP spherical micelles transitioned to form long fibers, as seen in FIG. 5A, diameter 32.9±4 nm, with a length extending over a few microns). Importantly, this observation confirms that minuscule structural perturbations in the terminal fragments of lipid lead to divergent energy landscapes for these lipoproteins, thus encoding the observed hysteretic transition in nano- and meso-scale assembly of ADA-IDPP. Though the assembly of small amphiphilic molecules is very sensitive to structural perturbation, the divergence between M- and ADA-IDPP is surprising, considering the highly asymmetric nature of these lipoproteins. Encoding non-equilibrium phase behaviour in IDPPs is an emergent frontier in biomacromolecular engineering and often requires significant alteration to the sequence of polypeptide or fusion of domains with defined secondary structure. Encoding hysteresis using subtle molecular perturbations is believed to be unprecedented in the literature. The interaction of strategically placed organic azides with water may influence the cation of azides in bioconjugation and metabolic labelling, so additional studies are warranted to probe the generality of this concept and its underlying mechanism.

Incorporation of non-canonical lipids with reactive moieties into proteins ushers new opportunities in material design. The reactivity of the azide group was envisioned to couple two lipoproteins with a precise pattern of amphiphilicity. ADA-IDPP was reacted with a telechelic alkyne (dipropargyl ether) to produce a lipoprotein with bolaamphiphile architecture (BMT-IDPP$_2$) in which the hydrophobic lipid is flanked by two thermally responsive protein domains (FIG. 14-15). The synthesis of such sequence-defined and monodisperse giant bolaamphiphiles ($M_n$=72 kDa, PDI=1) is not possible with canonical lipids, as they lack reactive functional groups at both termini.

The self-assembly, seen in FIG. 5B, and phase behavior, seen in FIG. 16, of BMT-IDPP$_2$ was distinctively different from the ADA-IDPP, highlighting the importance of programmable amphiphilic regions accessible through ncPTM. Below LCST, BMT-IDPP$_2$ self-assembled into 14.1±3.0 nm nanoparticles (FIG. 17), which reversibly transitioned into bottle-brush structures, above LCST, as seen in FIG. 5B. These bottle-brush structures contain a thinner core (7.7±1.6 nm), consistent with the size of dimerized lipid domain) and 70-80 nm corona (FIG. 18). This programmable assembly was unique to the bolaamphiphile architecture as the control construct, prepared from the reaction of ADA-IDPP with propargyl alcohol, only formed small particles with an average diameter of 6.4±0.2 nm (FIG. 19).

Figure 6:
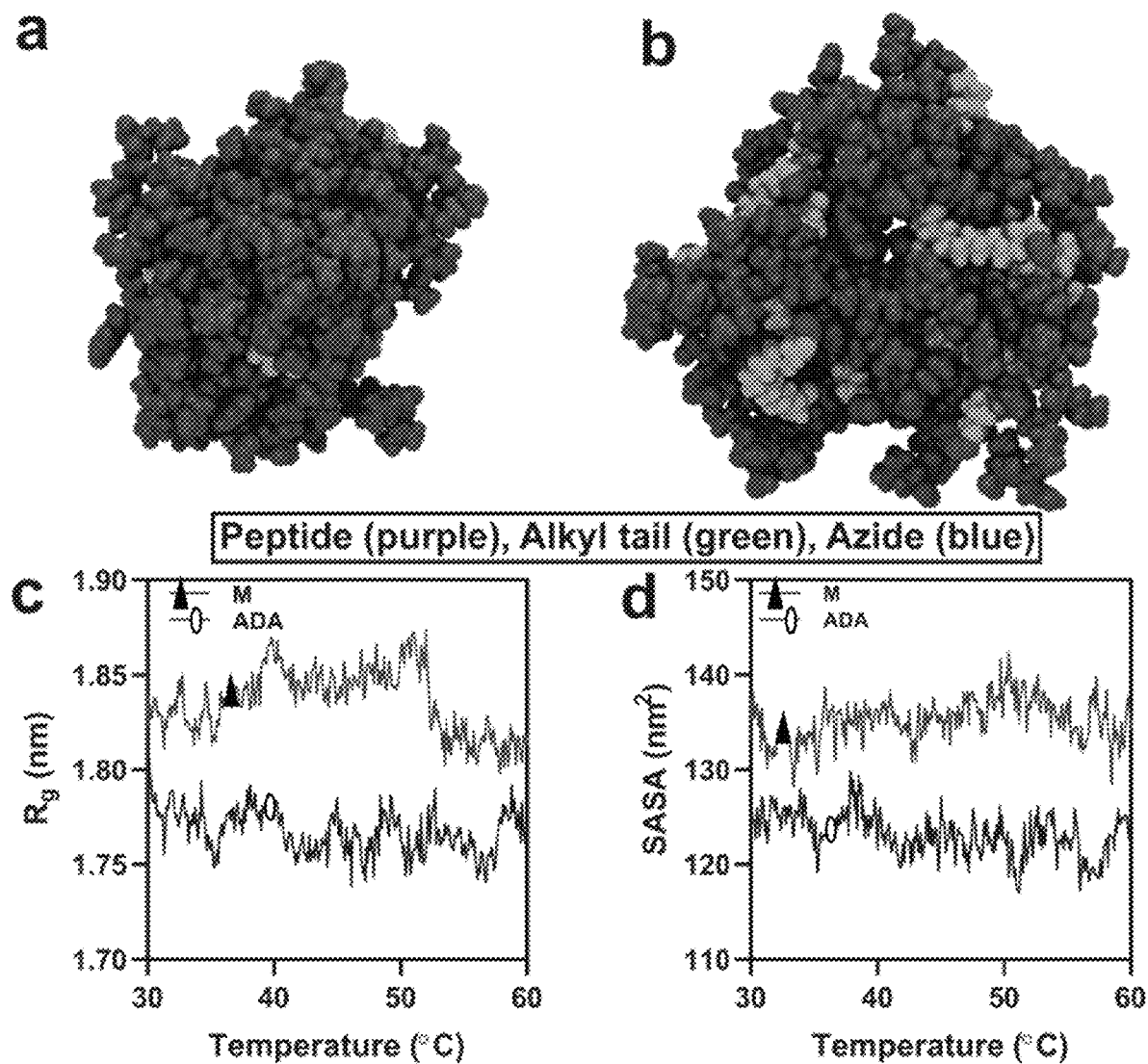
Figure 7:
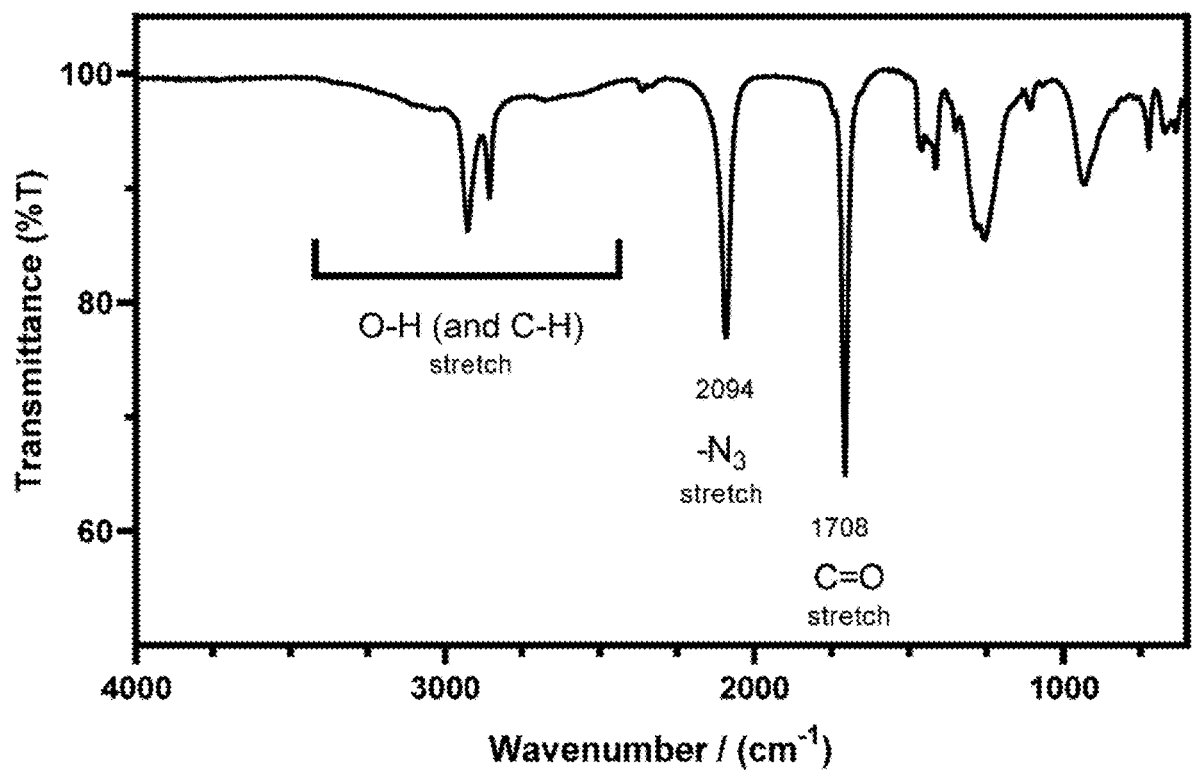
FIG. 7 is a graph of the attenuated Total Reflection Fourier Transform Infrared Spectroscopy (ATR-FT-IR) spectra of ADA.
Figure 8:
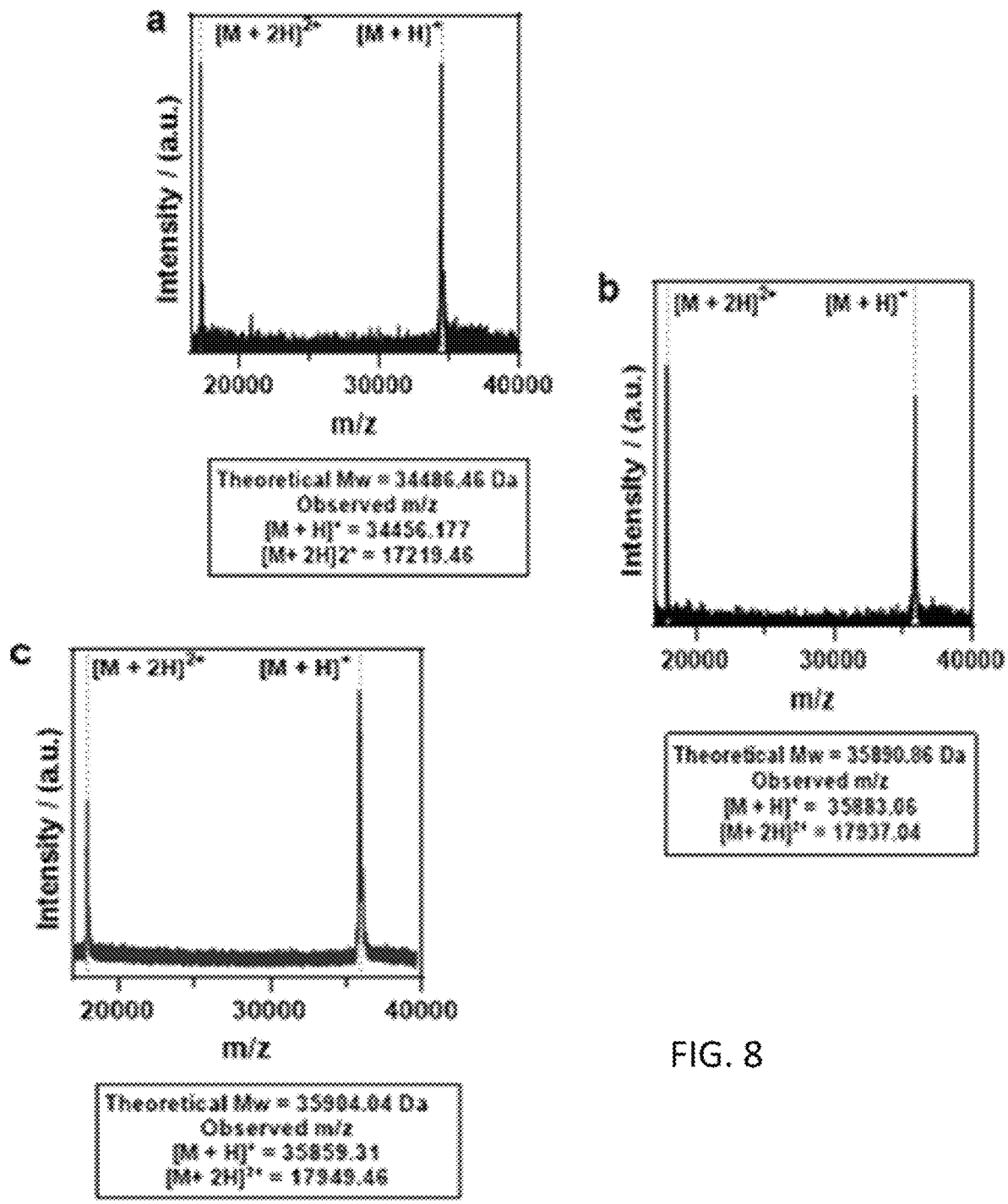
FIG. 8 is a series of graphs of the MALDI-TOF-MS of IDPP (a), M-IDPP (b), and ADA-IDPP (c) where vertical dashed lines denote theoretical molecular weight.

Finally, an in-silico model was developed to explain the differences in the assembly of M- and ADA-IDPP. Since 99.5% of two lipoproteins are identical, atomistic simulations were confined to to the N-terminal amphiphilic region (lipid-recognition sequence peptide). Using all-atom molecular dynamics simulations, the differences in the macromolecular assembly of M-peptide and ADA-peptide were captured. As shown in FIG. 6, M-peptides aggregate via the hydrophobic interactions of the myristoyl chains (green) that form a micellar core while the peptides (purple) form the shell, as seen in FIG. 6A. In contrast, in ADA-peptide assembly, seen in FIG. 6B, the polar azide groups (blue) are hydrophilic and remain solvent-exposed, preventing efficient packing and formation of a lipid core. The ADA-peptide aggregate has a consistently higher radius of gyration ($R_g$) and solvent accessible surface area (SASA) compared to M-peptide aggregate, as seen in FIGS. 6C and 6D, over the 30-60° C. The difference in packing efficiency is supported experimentally by the observed critical assembly concentration for ADA-IDPP (18 μM) and M-IDPP (2 μM), FIG. 20. The pathway-dependent differences between the assembly of M- and ADA-IDPP stem from the stability and dynamics of hydrophobic cores (FIG. 21). Though both lipoproteins form similar assemblies at low temperatures, the hydrophobic core of ADA-IDPP is more dynamic, lowering the energy barrier for the rearrangement of the IDPP chains at elevated temperatures.

The well-documented substrate-promiscuity of lipidation machinery has been extensively leveraged in the field of chemical biology. The present invention was used to design novel lipoproteins with emergent material properties such as stimuli-responsive shape-shifting nanomorphology. There are several opportunities for the design of dynamic nano-biomaterials in this untapped chemical design space. For example, the programmable morphological change from nanoparticles to fibers can be used to simultaneously release encapsulated cargo and provide a scaffold for cell-adhesion and growth. Non-canonical lipids can also be used as chemical handles for structural elaboration and synthesis of hybrid materials with unique and precise amphiphilic pattern. These hybrid systems can be programmed to assemble into complex 2D and 3D morphologies to form materials with unique optical and mechanical properties.

Example

Materials

The pETDuet-1 vector was purchased from EMD Millipore (Billerica, MA). The chemically competent Eb5alpha and BL21(DE3) cells, restriction enzymes, ligase, and corresponding buffers, as well as DNA extraction and purification kits, were purchased from New England Biolabs (Ipswich, MA). Isopropyl β-D-1-thiogalactopyranoside (IPTG) was purchased from A. G. Scientific (San Diego, CA). 12-bromododecanoic acid, apomyoglobin, adrenocorticotropic hormone (ACTH), sinapinic acid, alpha-cyano-4-hydroxycinnamic acid, copper(II) sulfate pentahydrate, (+)-sodium L-ascorbate, dipropargyl ether, propargyl alcohol, and trifluoroacetic acid (TFA) were purchased from Sigma-Aldrich (St. Louis, MO). High-performance liquid chromatography-(HPLC) grade acetonitrile, SnakeSkin™ dialysis tubing with 3.5K nominal molecular weight cut off (MWCO), mass spectroscopy grade Pierce™ trypsin protease, Tryptone, Yeast Extract, Sodium chloride, ampicillin, kanamycin, phosphate buffer saline (PBS), myristic acid, DMSO, Polyethylenimine (PEI), and ethanol were purchased from Thermo Fisher Scientific (Rockford, IL). Mini-PROTEAN® TGX Stain-Free™ Precast Gels, Precision Plus Protein™ All Blue Pre-stained Protein Standard, and Precision Plus Protein™ Unstained Protein Standards were purchased from Bio-Rad Laboratories, Inc. (Hercules, CA). AF488-DBCO was purchased from Fluroprobes (Scottsdale, AZ). The carbon-coated grid (CF300-Cu) was purchased from Electron Microscopy Sciences. Deionized water was obtained from a Milli-Q® system (Millipore SAS, France). Simply Blue™ SafeStain was purchased from Novex (Van Allen Way Carlsbad, CA). All chemicals were used as received without further purification.

Sequence of IDPP

N-myristoyl transferase from *Saccharomyces cerevisiae* (UniProtKB-P14743) was used in this example. The N-terminal peptide fragment of *S. cerevisiae* Arf2 (UniProtKB-P19146) GLYASKLFSNL (SEQ. ID NO: 1), was selected as the recognition sequence because of its high affinity for yeast NMT (Km~0.08 The high affinity of this peptide toward yeast NMT is advantageous because binding of ADA-CoA to NMT reduces the affinity of a model octapeptide toward NMT:ADA-CoA complex by 7-fold, compared to the natural substrate (M-CoA). The intrinsically disordered peptide-polymer that was fused to the peptide substrate sequence, comprised:

(SEQ. ID NO: 2)
GVGVPGVGVPGAGVPGVGVPGVGVPGVGVPGVGVPGAGVPGVGVPGVG

VPGGKGVGVPGVGVPGAGVPGVGVPGVGVPGVGVPGVGVPGAGVPGVG

VPGVGVPGGKGVGVPGVGVPGAGVPGVGVPGVGVPGVGVPGVGVPGAG

VPGVGVPGVGVPGGKGVGVPGVGVPGAGVPGVGVPGVGVPGVGVPGVG

VPGAGVPGVGVPGVGVPGGKGVGVPGVGVPGAGVPGVGVPGVGVPGVG

VPGVGVPGAGVPGVGVPGVGVPGGKGVGVPGVGVPGAGVPGVGVPGVG

VPGVGVPGVGVPGAGVPGVGVPGVGVPGGKGVGVPGVGVPGAGVPGVG

VPGVGVPGVGVPGVGVPGAGVPGVGVPGVGVPGGKGVGVPGVGVPGAG

VPGVGVPGVGVPGVGVPGVGVPGAGVPGVGVPGVGVPGGKGY

Synthesis of 12-azidododecanoic acid (ADA) was conducted by modifying existing literature procedures. Briefly, 12-bromododecanoic acid (400 mg, 1.43 mmol, 1 equiv.) was mixed with sodium azide (465 mg, 7.15 mmol, 5 equiv.) and DMF (10 mL). The heterogeneous reaction mixture was stirred for 12 h at 60° C. After cooling the reaction mixture, the solvent was evaporated in vacuo at 30° C. The remaining solid was dissolved in 20 mL deionized water and extracted with ethyl acetate (20 mL×3). The organic layer was washed with 0.1 M HCl (20 mL×3). The solvent was removed in vacuo to obtain the product as a white waxy solid. Yield: 87%. $^1$H-NMR (400 MHz, CDCl$_3$): δ [ppm]=3.29 (t, 2H, N$_3$—CH$_2$), 2.38 (t, 2H, CH$_2$—COOH), 1.65 (m, 4H), and 1.31 (m, 14H). $^{13}$C-NMR (100 MHz, CDCl$_3$): δ [ppm]= 180.30, 51.58, 34.23, 29.44, 29.42, 29.35, 29.19, 29.12, 29.02, 28.84, 26.70, 24.66.

Protein Expression, Post-Translational Modification, and Purification

Expression

Protein expression was conducted in BL21(DE3) strains. A 4 mL of sterile 2×YT medium with a corresponding antibiotic (ampicillin or kanamycin, see Table 1) was inoculated with a single bacterial colony. The culture was then shaken at 37° C. on an orbital shaker at 200 rpm. After overnight growth, this suspension was used to inoculate each 1 L of sterile 2×YT medium. The bacteria were grown in an orbital shaker incubator at 37° C. at 180 rpm. After reaching OD600~0.8, the culture media was supplemented with the fatty acid, myristic acid, or ADA, at the final concentration of 500 µM. After 15 min, expression was induced by the addition of IPTG to a final concentration of 1 mM. For non-myristoylated constructs, no myristic acid was added, and the protein expression was induced by adding IPTG to the culture at the OD of 0.8. The expression of proteins was then continued for 4 hours.

Note on optimization of expression condition: Devadas et al. quantified the substrate preference of NMT to accept ADA or M by quantifying the amount of modified peptide substrate (GARASVLS) using an in vitro end-point assay. In this assay, NMT exhibited a comparable preference for transferring ADA or M to this octapeptide. The observed comparable substrate preference involves the contribution of several opposing factors: (1) This assay requires activation of M or ADA to their corresponding acyl-CoA using *Pseudomonas* acyl-CoA synthetase. This enzyme exhibited a strong preference toward ADA over M and produced 1.5-2 times more ADA-CoA compared to M-CoA in vitro.; (2) NMT binds the peptide substrate only after binding acyl-CoA. In follow-up kinetic studies, NMT is shown to have a comparable affinity for M-CoA or ADA-CoA (Km=~4-6 µM). However, the binding of ADA-CoA reduced the NMT affinity for its peptide substrate. Km for the peptide was increased to 66 µM, compared to 9 µM for binding of the peptide NMT:Myr-CoA complex; (3) Once the ternary complex (NMT:acyl-CoA:Peptide) was formed, NMT exhibited higher efficiency in transferring the ADA-CoA to N-terminal glycine residue, Vm (ADA)=1.5×Vm (M).

Based on the kinetic data, NMT has a higher preference for M vs. ADA in vitro, using Vm/Km as a measure of catalytic efficiency. It should be noted that the apparent substrate preference of NMT inside *E. coli* is influenced by the intracellular pool of ADA-CoA and M-CoA. The concentration of these activated fatty acids is influenced by several (time-dependent) factors: (1) Transport of ADA across the cell envelope (diffusion or by fatty acid transporter, FadL); (2) The preference of *E. coli* acyl-CoA synthetase (FadD) to accept ADA as a substrate; (3) The intracellular pool of Myr-CoA from the endogenous fatty acid biosynthesis pathway; (4) Possible degradation ((3-oxidation) of ADA-CoA in the fatty acid degradation pathway; (5) Basal expression of NMT an IDPP in cells before induction and addition of ADA.

Additionally, it could not be ruled out that differences in the polypeptide substrate further change the kinetics of acyl transfer in vivo. The N-terminal sequence of Arf2 fused to a large IDPP was used in the experiment, but Devadas et al. used a short octapeptide derived from Pr55gag polypeptide precursor of human immunodeficiency virus I.

It was noted that the relative concentration of ADA-IDPP vs. M-IDPP decreases with the induction time. Therefore, a higher concentration of ADA was used in the expression culture and the expression time was reduced.

Purification

The cells were harvested by centrifugation at 3745×g at 4° C. for 30 min. The bacterial pellet was resuspended in phosphate buffer saline (PBS, 15 mL per 1 L of expression culture). The cells were then lysed by two rounds of sonication (10 s on, 60 s off, total sonication time of 90 s. Power: 60-80 w). To ensure complete dissipation of the heat generated during sonication cycles, the sample was kept on ice for 10 min after each cycle. Polyethylenimine was then added to the lysed culture (2 mL of 50% w/v solution per 1 L of expression culture) to remove the DNA fragments. The lysed bacterial solution was centrifuged (22,830×g, 4° C., 15 min) to separate the protein from insoluble cell debris and PEI-complexed nucleic acids. IDPP, M-IDPP, and ADA-IDPP were then purified from the endogenous *E. coli* proteins by leveraging their temperature-triggered liquid-liquid phase separation using inverse transition cycling.[5] Each protein was further purified by preparative HPLC to ensure purity (>95%) for the self-assembly studies. Reverse-phase HPLC (RP-HPLC) was performed with a Shimadzu HPLC system (Phenomenex Jupiter® 5 µm C4 300 Å, LC Column 250×10 mm, solvent A: H$_2$O+0.1% TFA, solvent B: acetonitrile+0.1% TFA). The percentage of the organic solvent in the mobile phase was increased from 0 to 90% over the course of 35 minutes. After HPLC purification, the organic solvent was removed by dialysis against water using Snake-Skin™ Dialysis Tubing (7000 MWCO, Thermo Scientific) overnight, followed by lyophilization. Lyophilized proteins were kept at −20° C. for long-time storage. Purified protein yield per L of culture: IDPP (~10 mg); M-IDPP (~8 mg); ADA-IDPP (~3-5 mg).

Synthetic Modification of ADA-IDPP

Synthesis of Bolaamphiphile (BMT-IDPP2)

Bolaamphiphile was synthesized by joining two ADA-IDPP chains via bis(methoxy-1,2,3-triazole), BMT, using a telechelic alkyne (dipropargyl ether), FIG. 15. ADA-IDPP (100 µM in water, 1.1 equiv) was mixed with dipropargyl ether (45 µM, 1.0 equiv) at room temperature. Aqueous solutions of CuSO4 and the accelerating ligand, tris(3-hydroxypropyltriazolylmethyl)amine (THPTA), were initially mixed in a separate tube for 5 minutes to form the THPTA-Cu2+ complex before addition to the reaction mixture (working concentrations: [CuSO4]=250 µM and [THPTA]=1.25 mM). The reaction was then started by adding sodium ascorbate to reduce the copper complex in situ to start the copper catalyzed alkyne azide cycloaddition (CuAAC). The progress of the reaction was monitored by using SDS-PAGE as well as analytical HPLC. After 3-6 hours, excess EDTA was added to the reaction mixture to stop the reaction. Bolaamphiphile construct was separated from excess ADA-IDPP using preparative HPLC. SDS-PAGE (FIG. 15b) and Analytical HPLC (FIG. 15c) were used to confirm the successful purification of BMT-IDPP2 (blue trace, tR=29.9 min) from excess ADA-IDPP (red trace, tR=31.1 min).

Given that the LCST of bolaamphiphile (and its concentration dependence) is identical to ADA-IDPP (Table 3), it was not attempted to purify these two proteins from the reaction mixture using traditional inverse transitional cycling, i.e., by adding kosmotropic salts to the mixture to trigger the LCST phase transition isothermally. However, it should be noted that unlike ADA-IDPP, bolaamphiphile undergoes a reversible phase transition at elevated temperatures (FIG. 3b and FIG. 15c). Consequently, it may be possible to separate IBMT-IDPP2 from the ADA-IDPP by thermal annealing at elevated temperatures. This condition results in the irreversible transition of ADA-IDPP into fibers with hysteric aggregation, which can then be separated from soluble BMT-IDPP2 constructs at temperatures below LCST.

Synthesis of the control hydroxylmethyl-1,2,3-triazole-IDPP (HMT-IDPP)

A control construct (HMT-IDPP, single-tail amphiphile in which the terminal azide is converted to a triazole moiety) was synthesized using CuAAC by reacting ADA-IDPP (100 µM, 1 equiv) with excess propargyl alcohol (1.0 mM, 10 equiv) using a reaction protocol described for BMT-IDPP2. HMT-IDPP was purified using HPLC, and its purity was confirmed using SDS-PAGE (FIG. 15b, lane 2) and analytical HPLC (FIG. 15c, tR=29.0).

Computational Method

The molecular structure of M-peptide and ADA-peptide molecules were built in two-steps. First, the three-dimensional structure of the recognition peptide (GLYASKLF-SNL) was determined using the I-TASSER webserver. In the second step, the M and ADA lipid tails were added to the glycine residue of the peptide using the CHARMM-GUI webserver. The individual M-peptide and ADA-peptide structures were equilibrated at 300 K using the CHARMM36 all-atom force field available within the CHARMM-GUI workspace.

The equilibrated structures were used to construct two explicitly solvated systems containing: (i) 15 molecules of M-peptide and (ii) 15 molecules of ADA-peptide. Each system contained 150 mM NaCl solution and TIP3P water molecules in a cubic box with a box length of 10 nm. The systems were energy minimized and equilibrated at T=300 K in the isothermal-isochoric (NVT) and at P=1 bar in isothermal-isobaric (NPT) ensemble constraints in the CHARMM-GUI workflow. The equilibrated output from these runs was used to study self-assembly behavior.

The self-assembly molecular dynamics simulations were performed using the GROMACS 2019.4 simulation package. The M-peptide and ADA-peptide molecules and ions were modeled using the CHARMM36 all-atom force field. Water was modeled using TIP3P. The NPT production runs were run for 400 ns using 2 fs timestep. The temperature was maintained at 303.15 K using the Nose-Hoover thermostat with τt=1.0 ps. The pressure was maintained at 1 bar using isotropic coupling using Parrinello-Rahman barostat with τP=5 ps and compressibility of 4.5×10-5 bar-1. Periodic boundary conditions were applied in all three dimensions. The nonbonded van der Waals interactions were calculated using a cutoff of 1.2 nm. The long-range electrostatic interactions were studied with particle mesh Ewald (PME) algorithm at a 1.2 nm cutoff. Further, the behavior of the system during the heating cycle was simulated for both systems over 280-360 K temperature range (280, 290, 300, 310, 320, 330, 340, 350, and 360 K) over a total simulation time of 400 ns. Analyses of the results from thermal annealing simulations, including radius of gyration (Rg) and solvent accessible surface area (SASA), were performed using GROMACS built-in utilities. Molecular visualization was performed using VMD software.

Characterization

Fourier Transform Infrared Spectroscopy

Fourier transform infrared spectroscopy (FT-IR) spectra were obtained on a Bruker Tensor 27 spectrophotometer with a MIR source and a DLaTGS detector. Spectra were recorded under ambient conditions at a resolution of 4 cm-1. A total of 64 scans were recorded for each spectrum in addition to the background.

Sodium Dodecyl Sulfate Polyacrylamide Gel Electrophoresis (SDS-PAGE)

The purity, molecular weight, and fluorescent labelling of the purified proteins were first assessed using SDS-PAGE (10% cross-linked. TGX Stain-Free™ gels). The gels with fluorescently labelled proteins (see below) were initially visualized using a blue LED transilluminator (□ex=465 nm) followed by visualization under UV-light (□ex=350 nm) using a BioRad Gel Doc EZ imager. The gels were then stained with SimplyBlue™ SafeStain by following the manufacturer protocol and imaged using BioRad Gel Doc EZ imager.

Fluorescent Labelling

Strain-promoted alkyne-azide cycloaddition reaction was used to selectively label the proteins bearing bioorthogonal azide group (ADA-IDPP). Alexa Fluro 488 fluorophore conjugated to Dibenzocyclooctyne (AF488-DBCO) was dissolved in DMSO at the final concentration of 1 mg/mL. Protein solution (~25 μM, 10 μL) of ADA-IDPP or M-IDPP were mixed AF488-DBCO (~1.05 mM, 4 μL) in an Eppendorf tube. The reaction mixture was kept in the dark at room temperature on a tube rotator overnight. The proteins were then separated from unreacted AF488-DBCO using SDS-PAGE. The labelled protein bands were visualized as described above. Total protein content was assayed by staining the gel with SimplyBlue.

Analytical HPLC

Analytical RP-HPLC was performed on a Shimadzu instrument using a Phenomenex Jupiter® 5 μm C4 300 Å, 250×4.6 mm LC Column with a mobile phase consisting of a gradient of acetonitrile in water (Table 2) to analyze IDPP, M-IDPP, and ADA-IDPP, FIG. 2a. HMT-IDPP and BMT-IDPP2 were analyzed by a Phenomenex Jupiter® 5 μm C18 300 Å, 250×4.6 mm LC Column using the solvent gradient in Table 2 (FIG. 15c). The proteins were analyzed using a photodiode array detector at wavelengths between 190 and 800 nm.

TABLE 2

The gradient mobile phase composition of analytical HPLC.

| Time (min) | % B (CH3CN + 0.1% TFA) |
|---|---|
| 0 | 0 |
| 5 | 0 |
| 45 | 90 |

Matrix Assisted Laser Desorption/Ionization Time-of-Flight Mass Spectrometry (MALDI-TOF-MS)

MALDI-TOF-MS was conducted on Bruker Autoflex III with smart ion source. A saturated solution of sinapinic acid in 30% acetonitrile was used as the matrix. Samples for MALDI-TOF-MS analysis were prepared by mixing 2 μL of the protein solutions (50 μM) with the matrix (8 μL), followed by serial dilution. These solutions were plated onto a sample plate and dried at room temperature. Apomyoglobin (MW=16,952.27 Da) was used as standard.

Trypsin Digestion of Proteins

To confirm the regioselectivity of lipid modification, proteins were digested with trypsin, and the peptide fragments were analyzed using MALDI-TOF-MS. Trypsin digestion was conducted according to the manufacturer's protocol. Briefly, 9 μL of protein (50 μM in PBS) was added to 10 μL of 50 mM ammonium bicarbonate buffer (pH=7.8) in an Eppendorf tube. To this mixture, 1 μL trypsin (reconstituted as 1 μg/μL in 50 mM acetic acid) was added, and the reaction mixture was incubated at 37° C. After 3 h, the peptide fragments were analyzed by MALDI-TOF-MS. α-cyano-4-hydroxycinnamic acid was used as a matrix and adrenocorticotropic hormone (Mw=2,464.1989 Da) was used as calibrant for the analysis of the trypsin-digested peptide fragments.

Turbidimetry Assay

Temperature-triggered phase separation of IDPP, M-IDPP, and ADA-IDPP were monitored using an Agilent UV-Vis Spectrophotometer (Cary100) equipped with a Peltier temperature controller by measuring the optical density of the solution at 350 nm (where all proteins had negligible extinction coefficients). Proteins were dissolved in PBS in three concentrations (50, 25, and 12.5 μM) and were equilibrated at 20° C. (below the transition temperature of all constructs) for 5 minutes before heating the solution at the rate of 1° C./min. M-IDPP, ADA-IDPP, HMT-IDPP, and BMT-IDPP2 were heated to 45° C., while unmodified IDPP was heated to 60° C. as it had a higher transition temperature. At the end of the heating cycle, the protein solutions were cooled at the rate of 1° C./min to 20° C. while monitoring the optical density at 350 nm. The transition temperatures were calculated by the method of first derivative using the optical density plotted against the temperature. Transition temperatures are defined as the inflection point (the maximum of the first derivative) in the optical density during the heating cycle. These data were fitted to the following model Tt=−m×ln [IDPP]+Tc to derive critical transition temperature (Tc) and the concentration dependence of Tt (m), summarized in Table 3.

TABLE 3

Critical transition temperature (Tc) and the concentration dependence of Tt derived from turbidity plots.

| Construct | m (90% CI)[a] | Tc (90% CI)[b] |
|---|---|---|
| IDPP | 5.3 (2.8-7.9) | 65.9 (57.6-74.2) |
| M-IDPP | 1.1 (0.4-1.8) | 37.1 (34.7-39.6) |
| ADA-IDPP | 1.3 (0.4-2.2) | 36.4 (33.4-39.4) |

TABLE 3-continued

Critical transition temperature (Tc) and the concentration
dependence of Tt derived from turbidity plots.

| Construct | m (90% CI)[a] | Tc (90% CI)[b] |
|---|---|---|
| HMT-IDPP | 2.9 (1.5-4.4) | 45.6 (41.9-49.4) |
| BMT-IDPP2 | 1.4 (0-2.8) | 35.1 (31.5-38.7) |

Derived values from fitting the Tt data to the following model: Tt=−m×ln ([IDPP])+Tc. [a] ° C./ln (μM/μM). [b] ° C. 90% confidence intervals are calculated from the linear regression analysis using Graphpad prism 8.4.

Dynamic Light Scattering (DLS)

DLS experiments were conducted on Zetasizer Nano (Malvern Instruments) with 173° backscatter detector. Protein samples in PBS (50 μM) were filtered through a Millex®-LH Low protein Binding Hydrophilic LCR Membranes (0.45 μm) into the DLS cuvette. The measurements were conducted in triplicates at each temperature. The temperature was increased in 5° C. increments, and the samples were equilibrated at each temperature for 1 min. IDPP was analyzed in the temperature range of 15-60° C. (IDPP), and lipidated IDPP (M-IDPP and ADA-IDPP) were analyzed in the temperature range of 15-45° C. At the end of the heating cycle, the temperature was reduced to 15° C. Scattering correlation function was analyzed using the Zetasizer software using the method of cumulants and CONTIN to calculate the hydrodynamic radii of each construct at each temperature.

The size of IDPP unimer was estimated using the following equation17, which is a scaling law based on Flory's mean field approach18:

$$Rg = \sqrt{\frac{2l_p b}{(2v+1)(2v+2)}} N^v = 8.8 \text{ nm}$$

TABLE 4

Parameters used for estimation of the size of IDPP unimer.

| | Parameter | Value (unit) | Reference |
|---|---|---|---|
| lp | Persistence length = ½ Kuhn length (lk)* | 1.05 nm | 19 |
| b | Monomer size* | 0.365 nm | 19 |
| N | 3 × (number of pentapeptide repeat) | 240 | 20 |
| v | Flory exponent for the expanded coil state | ⅗ | 18 |

Transmission Electron Microscopy (TEM)

The TEM imaging was performed on JEOL-2100F operated at 200 kv and images were recorded by Gatan CCD camera. ADA-IDPP solution (10 μL) used in DLS experiment, i.e., after thermal annealing, were deposited onto carbon-coated grid (CF300-Cu, Electron Microscopy Sciences) or glow discharged carbon-coated copper grids for 5 minutes before blotting the excess solution. The grid was then stained with 10 μL of 1% uranyl acetate and the excess stain was blotted after 1 min. The grid was dried at room temperature for 2 hours followed by vacuum drying for 12 hours before imaging. BMT-IDPP2 solution was heated to 37° C. before depositing a 10 μL of the sample onto the TEM grid. Images of M-IDPP and ADA-IDPP (below LCST, FIG. 10) were obtained in a similar manner by dissolving the lyophilized protein in cold PBS just before deposition onto the grid.

Pyrene Assay

A pyrene assay was to determine the critical micellization concentration (CMC) of M-IDPP and ADA-IDPP at 20° C. (below transition temperature). The fluorescence of pyrene was measured using a Cary Eclipse Fluorescence Spectrophotometer at the excitation wavelength=334 nm. The emission signal was recorded between 350-450 nm, at 1 nm intervals with the scan rate of 600 nm/min.

Statistical Analysis

Statistical analysis was conducted using GraphPad Prism 8.4. The line representing the phase boundary between single-phase and two-phase regimes for each construct (FIG. 3d and FIG. 16b,d) was obtained by linear regression analysis of transition temperatures vs. natural log of concentration. The dashed band represents 90% confidence interval.

The error bars for all DLS measurements (FIG. 4b, FIG. 11, and FIG. 19c) represent standard deviation of three measurements. Two-way Analysis of Variance (ANOVA) in FIG. 4b was conducted using GraphPad prism software.

TEM images were analyzed using Fiji to determine the width of fibers. The result is reported as average±standard deviation as well as the frequency distributions. The sample size is reported in parenthesis.

What is claimed is:

1. A method of synthesizing a non-naturally occurring lipoprotein, comprising the steps of:
   modifying a host organism to express a *Saccharomyces cerevisiae* N-myristoyl transferase;
   modifying the host organism to express an intrisincally disordered peptide polymer fused to a peptide substrate of the N-myristoyl transferase; and
   coexpressing the N-myristoyl transferase and the intrinsically disordered peptide polymer from the host organism in the presence of an expression media having a non-natural fatty acid having the formula R—COOH, where R contains a linear chain of no more than 15 atoms of C, N, O or S, so that the intrinsically disordered peptide polymer fused to the peptide substrate is subjected to post-translational modification by the host organism to form a non-naturally occurring lipoprotein.

2. The method of claim 1, wherein the peptide substrate comprises SEQ ID NO: 1.

3. The method of claim 2, wherein the non-natural fatty acid is a non-natural substrate of the N-myristoyl transferase.

4. The method of claim 2, wherein the non-natural fatty acid is an analogue of myristic acid.

5. The method of claim 4, wherein the non-natural fatty acid is 12-azidododecanoic acid.

6. The method of claim 5, wherein the non-naturally occurring lipoprotein comprises a canonical post translational modification.

7. The method of claim 5, wherein the non-naturally occurring lipoprotein comprises non-canonical post translational modifications.

8. The method of claim 5, wherein the intrinsically disordered peptide-polymer comprises SEQ ID NO: 2.

* * * * *